US011083619B2

(12) United States Patent
Hall et al.

(10) Patent No.: US 11,083,619 B2
(45) Date of Patent: Aug. 10, 2021

(54) ORGANIC LED LIGHT AND ULTRASONIC TRANSDUCER DEVICE IN A FLEXIBLE LAYER CONFIGURATION WITH ELECTRICAL STIMULATION

(71) Applicant: CAREWEAR CORP., Reno, NV (US)

(72) Inventors: Michael R. Hall, Lawrence, KS (US); John C. Castel, Reno, NV (US); Dawn Castel, Reno, NV (US)

(73) Assignee: CAREWEAR CORP., Reno, NV (US)

( * ) Notice: Subject to any disclaimer, the term of this patent is extended or adjusted under 35 U.S.C. 154(b) by 400 days.

(21) Appl. No.: 15/382,795

(22) Filed: Dec. 19, 2016

(65) Prior Publication Data

US 2017/0100585 A1 Apr. 13, 2017

Related U.S. Application Data

(63) Continuation of application No. 14/213,999, filed on Mar. 14, 2014, now Pat. No. 9,561,357.

(Continued)

(51) Int. Cl.
*A61F 7/00* (2006.01)
*A61N 7/00* (2006.01)
(Continued)

(52) U.S. Cl.
CPC .......... *A61F 7/007* (2013.01); *A61M 37/0092* (2013.01); *A61N 1/0432* (2013.01);
(Continued)

(58) Field of Classification Search
CPC ........ A61N 1/328; A61N 1/30; A61N 5/0616; A61N 1/0452; A61N 1/0432;
(Continued)

(56) References Cited

U.S. PATENT DOCUMENTS 4,780,212 A 10/1988 Kost et al.
5,656,015 A * 8/1997 Young .................. A61N 7/00
601/2

(Continued)

FOREIGN PATENT DOCUMENTS

EP 1 774 920 A1 4/2007
JP 1991(H03)-170172 A 7/1991
(Continued)

OTHER PUBLICATIONS

Yamae et al., *High-Efficiency White OLEDs with Built-up Outcoupling Substrate*, SID Symposium Digest of Technical Papers 42 (2012) (4 pgs).

(Continued)

*Primary Examiner* — Serkan Akar
(74) *Attorney, Agent, or Firm* — Stinson LLP

(57) ABSTRACT

A flexible device having a layered structure for delivering electrical stimulation and one or both of light and ultrasound to a skin surface is provided. The device is flexible so as to form a non-planar contact surface against the skin surface, and includes one or both of (a) a flexible light emitter layer positioned between two flexible conductive layers that emits light when driven by a power source and (b) a flexible ultrasound emitter layer positioned between two flexible conductive layers that produces ultrasound when driven by a power source. The device also includes a flexible electrical stimulation layer that functions as an electrode and is configured to provide electrical stimulation when driven by a power source.

46 Claims, 16 Drawing Sheets

Related U.S. Application Data

(60) Provisional application No. 61/799,153, filed on Mar. 15, 2013.

(51) Int. Cl.

| | | |
|---|---|---|
| *A61N 5/06* | (2006.01) | |
| *A61N 1/32* | (2006.01) | |
| *A61N 1/04* | (2006.01) | |
| *A61N 1/36* | (2006.01) | |
| *A61M 37/00* | (2006.01) | |
| *A61N 1/30* | (2006.01) | |
| A61F 7/02 | (2006.01) | |

(52) U.S. Cl.
CPC .............. *A61N 1/0452* (2013.01); *A61N 1/30* (2013.01); *A61N 1/328* (2013.01); *A61N 1/3603* (2017.08); *A61N 5/0613* (2013.01); *A61N 5/0616* (2013.01); *A61N 7/00* (2013.01); *A61F 2007/0052* (2013.01); *A61F 2007/0071* (2013.01); *A61F 2007/0261* (2013.01); *A61N 2005/0653* (2013.01); *A61N 2007/0034* (2013.01); *A61N 2007/0073* (2013.01)

(58) Field of Classification Search
CPC .... A61N 1/36014; A61N 5/0613; A61N 7/00; A61N 2005/0653; A61N 2007/0073; A61N 2007/0034; A61F 7/007; A61F 2007/0261; A61F 2007/0071; A61F 2007/0052; A61M 37/0092
See application file for complete search history.

(56) References Cited

U.S. PATENT DOCUMENTS

| | | | |
|---|---|---|---|
| 6,234,990 | B1 | 5/2001 | Rowe et al. |
| 6,396,199 | B1 | 5/2002 | Douglas et al. |
| 6,622,049 | B2 | 9/2003 | Penner et al. |
| 7,133,710 | B2 | 11/2006 | Acosta et al. |
| 7,273,457 | B2 | 9/2007 | Penner |
| 7,777,416 | B2 | 8/2010 | Chari et al. |
| 8,373,341 | B2 | 2/2013 | Xue et al. |
| 8,384,630 | B2 | 2/2013 | Ray et al. |
| 8,415,879 | B2 | 4/2013 | Lowenthal et al. |
| 9,061,128 | B2 | 6/2015 | Hall et al. |
| 9,561,357 | B2 | 2/2017 | Hall et al. |
| 2001/0031922 | A1 | 10/2001 | Weng et al. |
| 2002/0082668 | A1 | 6/2002 | Ingman |
| 2003/0023270 | A1 | 1/2003 | Danz et al. |
| 2004/0030267 | A1 | 2/2004 | Orten |
| 2004/0166146 | A1 | 8/2004 | Holloway et al. |
| 2004/0171980 | A1 | 9/2004 | Mitragotri et al. |
| 2004/0260217 | A1 | 12/2004 | Gardner et al. |
| 2005/0080465 | A1 | 4/2005 | Zelickson et al. |
| 2005/0137656 | A1 | 6/2005 | Malak |
| 2005/0177093 | A1 | 8/2005 | Barry et al. |
| 2006/0167531 | A1 | 7/2006 | Gertner et al. |
| 2006/0173514 | A1 | 8/2006 | Biel et al. |
| 2006/0253078 | A1 | 11/2006 | Wu et al. |
| 2006/0293727 | A1 | 12/2006 | Spooner |
| 2007/0149868 | A1 | 6/2007 | Blank et al. |
| 2007/0208395 | A1 | 9/2007 | Leclerc et al. |
| 2007/0247061 | A1 | 10/2007 | Adamovich et al. |
| 2008/0051680 | A1 | 2/2008 | Luebcke |
| 2008/0097557 | A1* | 4/2008 | Eggers ................ A61B 18/082 607/99 |
| 2008/0146890 | A1 | 6/2008 | LeBoeuf et al. |
| 2008/0215039 | A1 | 9/2008 | Slatkine et al. |
| 2008/0232088 | A1 | 9/2008 | Hente |
| 2008/0243049 | A1 | 10/2008 | Hardy |
| 2009/0099482 | A1 | 4/2009 | Furuhata |
| 2009/0130190 | A1 | 5/2009 | Breitenbach et al. |
| 2009/0259176 | A1 | 10/2009 | Yairi |
| 2010/0069898 | A1 | 3/2010 | O'Neil et al. |
| 2010/0100160 | A1 | 4/2010 | Edman et al. |
| 2010/0152644 | A1 | 6/2010 | Pesach |
| 2010/0179469 | A1 | 7/2010 | Hammond et al. |
| 2010/0204617 | A1 | 8/2010 | Ben-Ezra |
| 2010/0217100 | A1 | 8/2010 | LeBoeuf et al. |
| 2010/0217102 | A1 | 8/2010 | LeBoeuf et al. |
| 2010/0253225 | A1 | 10/2010 | Lifka et al. |
| 2010/0256489 | A1 | 10/2010 | Pedersen et al. |
| 2010/0292632 | A1 | 11/2010 | Mulvihill et al. |
| 2011/0034972 | A1 | 2/2011 | Samuel |
| 2011/0040235 | A1 | 2/2011 | Castel |
| 2011/0071482 | A1 | 3/2011 | Selevan |
| 2011/0082412 | A1 | 4/2011 | Hyde et al. |
| 2011/0178441 | A1 | 7/2011 | Tyler |
| 2011/0224598 | A1 | 9/2011 | Barolet |
| 2012/0157804 | A1 | 6/2012 | Rogers et al. |
| 2012/0161113 | A1 | 6/2012 | Lowenthal et al. |
| 2012/0172951 | A1 | 7/2012 | Choi |
| 2012/0267986 | A1 | 10/2012 | Galluzzo et al. |
| 2012/0277639 | A1 | 11/2012 | Pollock et al. |
| 2013/0006119 | A1 | 1/2013 | Pan et al. |
| 2013/0041235 | A1 | 2/2013 | Rogers et al. |
| 2013/0124039 | A1 | 5/2013 | Abreu |
| 2013/0306971 | A1* | 11/2013 | Bedell ..................... H01L 21/84 257/59 |
| 2014/0128798 | A1 | 5/2014 | Janson et al. |
| 2014/0155679 | A1 | 6/2014 | Pesach et al. |
| 2017/0100585 | A1 | 4/2017 | Hall et al. |

FOREIGN PATENT DOCUMENTS

| | | |
|---|---|---|
| JP | 1996(H08)-098863 A | 4/1996 |
| JP | 2005-520583 A | 11/2002 |
| JP | 2008-500846 A | 4/2005 |
| JP | 2011-509756 A | 3/2011 |
| JP | 2012-501799 A | 1/2012 |
| JP | 2012-514498 A | 6/2012 |
| WO | WO 1995/03744 A1 | 2/1995 |
| WO | WO 2000/078232 A1 | 12/2000 |
| WO | WO 2004/016311 A2 | 2/2004 |
| WO | WO 2007/054855 A1 | 5/2007 |
| WO | WO 2011/110277 A1 | 9/2011 |
| WO | WO 2011/135362 A1 | 11/2011 |
| WO | WO 2012/010238 A1 | 1/2012 |
| WO | WO 2012/025399 A1 | 3/2012 |
| WO | WO 2012/031092 A2 | 3/2012 |
| WO | WO 2012/031178 A2 | 3/2012 |
| WO | WO 2012/092057 A1 | 7/2012 |
| WO | WO 2014/075101 A1 | 5/2014 |
| WO | WO 2014/118571 A1 | 8/2014 |

OTHER PUBLICATIONS

Komoda et al., *High Efficiency Light OLEDS for Lighting*, J. Photopolymer Science and Technology, vol. 25, No. 3 (2012) (6 pgs).

Klimowicz, *Evaluation of Skin Penetration of Topically Applied Drugs in Humans by Cutaneous Microdialysis*, J Clin Pharm Ther. Apr; 32(2) (2007) (4 pgs).

Ault et al., *Microdialysis Sampling for the Investigation of Dermal Drug Transport*, Pharm Res. Oct 9 (10): (1992) (6 pgs).

International Search Report and Written Opinion for related application, PCT/US2014/029526, dated Aug. 18, 2014 (15 pgs).

Ashkenazi et al., "Eradication of Propionibacterium acnes by its endogenic porphyrins after illumination with high intensity blue light", FEMS Immunology and Medical Microbiology 35 (2003) 17-24. (Year: 2003) (8 pgs).

\* cited by examiner

ORGANIC LED LIGHT AND ULTRASONIC TRANSDUCER DEVICE IN A FLEXIBLE LAYER CONFIGURATION WITH ELECTRICAL STIMULATION

CROSS-REFERENCE TO RELATED APPLICATIONS

This continuation application is based on and claims priority to U.S. patent application Ser. No. 14/213,999, filed on Mar. 14, 2014, which claims priority to U.S. Provisional Application Ser. No. 61/799,153, filed on Mar. 15, 2013, each of which is incorporated herein by reference in its entirety.

STATEMENT REGARDING FEDERALLY SPONSORED RESEARCH OR DEVELOPMENT

Not applicable.

BACKGROUND OF THE INVENTION

Various devices for delivering light and/or ultrasound to the skin of a patient for therapeutic or cosmetic purposes are known in the art. In general, these devices do not provide uniform light and/or a uniform ultrasound field across the surface of the device. For example, when conventional light emitting diodes (LEDs) are used as a light source, each LED operates as a point source that can generate a hot spot if positioned too close to the patient's skin. Also, because typical LEDs have a relatively large beam divergence (e.g., about 65 degrees on each side for a total of 130 degrees), the light field is not uniform unless the LEDs are positioned a sufficient distance from the tissue. As another example, many conventional ultrasonic transducers have a beam non-uniformity ratio (i.e., the ratio between peak intensity and average intensity in the beam) of 5 to 6 or higher. As a result, the intensity of the ultrasound varies across the surface of the device.

BRIEF SUMMARY OF THE INVENTION

A device for delivering light and ultrasound across a skin surface is provided. The device has a layered structure comprising a light source and an ultrasonic transducer supported by a substrate. The light source comprises a flexible light emitter layer electrically coupled to a first conductive layer and a second conductive layer, wherein at least one of the first and second conductive layers is transparent. The ultrasonic transducer comprises a flexible ultrasound emitter layer electrically coupled to a third conductive layer and a fourth conductive layer. In an exemplary embodiment, the light source comprises one of an organic light emitting diode or a plurality of printed light emitting diodes and the ultrasonic transducer comprises a piezoelectric coating (film or paint). The device may optionally include a flexible transparent heater layer and/or an electrical stimulation layer. Preferably, the device is very thin and has a thickness of about 3 mm or less, and is flexible and conformable so as to form a non-planar contact surface against the skin surface.

The light source produces light with an intensity that is substantially uniform across the surface of the device. Similarly, the ultrasonic transducer produces ultrasound with an intensity that is substantially uniform across the surface of the device. Preferably, the ultrasound produced across the surface of the device has a beam non-uniformity ratio of 3 or lower. The ultrasonic transducer produces low frequency ultrasound at a frequency in the range of 2 kHz to 500 kHz and/or high frequency ultrasound at a frequency in the range of 500 kHz to 20 MHz. In one embodiment, the ultrasonic transducer is a dual frequency ultrasound transducer that produces both low frequency ultrasound and high frequency ultrasound either simultaneously or sequentially. The light source and ultrasonic transducer are capable of delivering light and ultrasound, respectively, in a pulsed mode or a continuous mode.

In some embodiments, the device is electronically coupled to a controller, which is also electrically coupled to one or more sensors. The controller is operable to receive sensor data from the sensor and dynamically control the device in response to the received sensor data. In one embodiment, the controller dynamically adjusts an operating parameter of the device in response to the received sensor data. For example, the controller may independently control the light source by adjusting the activation and deactivation of the light source, voltage, current, light wavelength, pulse width, modulation frequency, duty factor, or light treatment time. As another example, the controller may independently control the ultrasonic transducer by adjusting the activation and deactivation of the transducer, ultrasound treatment time, ultrasound frequency, or ultrasound modulation frequency.

In some embodiments, the controller is electrically coupled to a communication module that enables wired or wireless communication with an external control device. The external control device may comprise, for example, a smart phone, a tablet computer, or a laptop computer. The external control device is capable of executing a control application for externally controlling the controller. The external control device may in turn communicate over a communication network (e.g., the Internet cloud) in order to access applications or data hosted on a remote server to modify one or more treatment parameters based on information stored on the remote server.

In a preferred aspect, the light and ultrasound emitted from the device causes transdermal transport of a therapeutic or cosmetic composition through the skin surface. In one embodiment, the therapeutic or cosmetic composition includes one or more of large or small molecular weight hyaluronic acid, ascorbic acid (vitamin C) or alpha-tocopherol (vitamin E) or their derivatives or their pharmaceutically acceptable salts and esters.

DETAILED DESCRIPTION OF EXEMPLARY EMBODIMENTS

The present invention is directed to a flexible device that provides light energy and/or ultrasound in the form of a very thin layered structure. The overall thickness of the device is typically about 10 mm or less (e.g., about 10, 9, 8, 7, 6, 5, 4, 3, 2, 1, 0.5, 0.4, 0.3, 0.2, 0.1, 0.05 mm or less). The device comprises at least one flexible light source for providing light and/or at least one flexible ultrasonic transducer for providing ultrasound. Among other things, the device can be used for transdermal drug delivery, cosmetic applications, and skin/wound healing. An advantage of the device is that the light energy and/or ultrasound produced by the device is substantially constant across the surface of the device. Another advantage is that the device is flexible and may be contoured in any shape and size allowing the device to conform to any body surface due to the layered/stacked nature of the films/layers forming the light source and/or ultrasonic transducer of the device. A further advantage of the device is that is can be manufactured at a relatively low cost and, thus, the device may be disposable. The device may optionally be controlled by an electronic circuit with one or more sensors that operate in a closed loop to provide feedback to a microcontroller for dose control.

Figure 1:
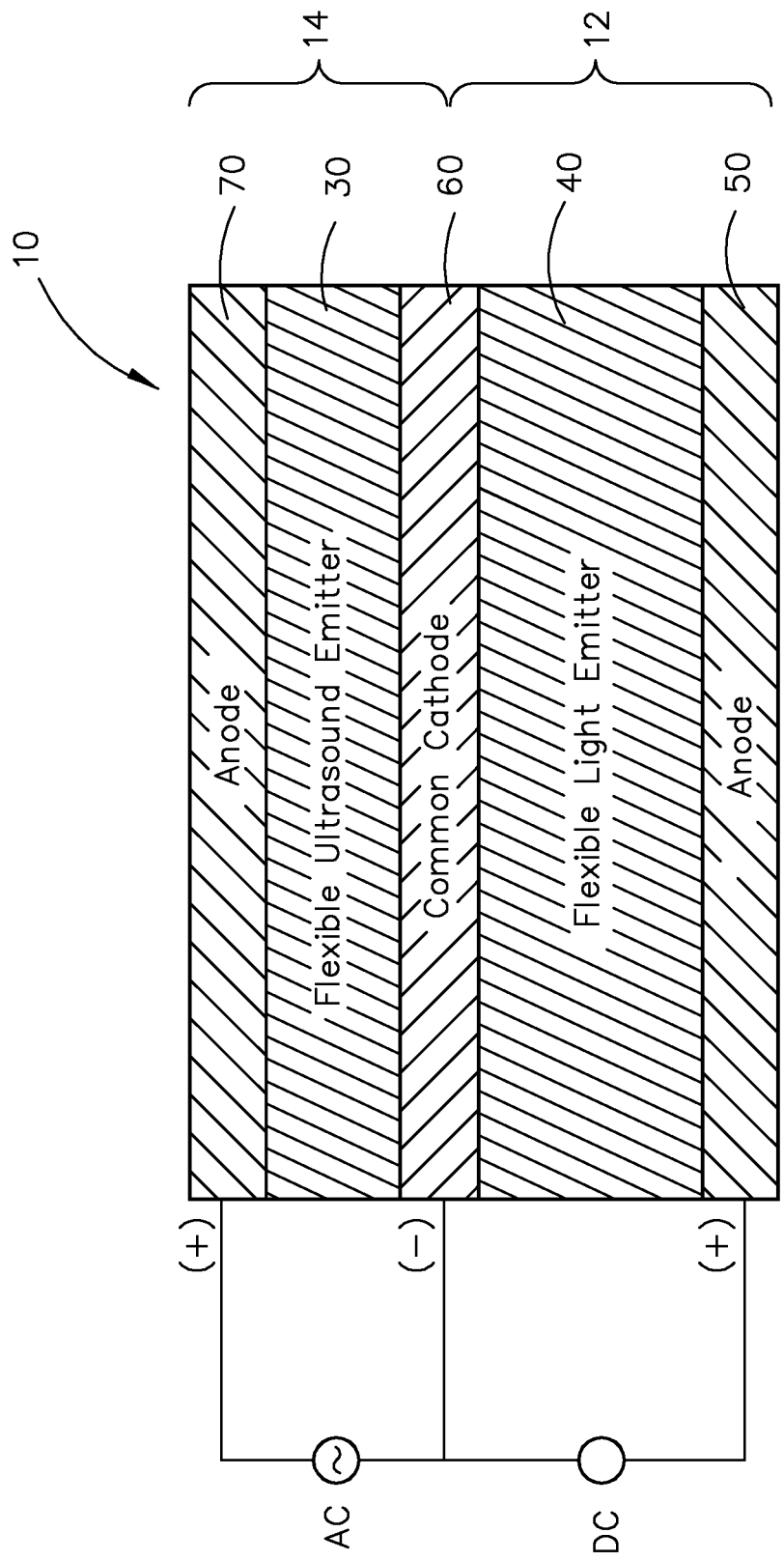
FIG. 1 illustrates the general structure of a device that provides light and ultrasound in the form of a very thin layered structure in accordance with the present invention.

FIG. 1 illustrates the basic elements of the device of the present invention in the form of a thin layered structure. The device 10 comprises a light source 12 and an ultrasonic transducer 14. The light source 12 comprises a flexible light emitter 40 located between an anode 50 and a cathode 60. The ultrasonic transducer 14 comprises a flexible ultrasound emitter 30 located between the cathode 60 and an anode 70. The cathode 60 is a common cathode for both the light source 12 and the ultrasonic transducer 14. Suitable power sources are connected to the device 10. Preferably, direct current (DC) or pulsed DC is used to power the light source 12, while alternating current (AC) is used to power the ultrasonic transducer 14.

The light source of the present invention produces light with an intensity that is substantially constant across the surface of the device so as to provide substantially uniform light emission when the device is in contact with the patient's skin. As described in more detail below, the light source may comprise, for example, organic light emitting diodes (OLEDs) or printable light emitting diodes (LEDs) (organic or inorganic) commonly referred to as LED ink. With OLEDs, the intensity of the light is substantially constant across the surface of the device due to the relatively uniform deposition of organic material on a substrate during fabrication of the OLED. With LED ink, each light source is very small which enables the LEDs to be positioned in very close proximity to each other. During fabrication, the LEDs may be printed in a uniform manner whereby each LED operates as a point source in which the beams from the individual LEDs are substantially parallel to each other to provide substantially uniform light across the surface of the device. Unlike conventional LEDs, the light source of the present invention does not need to be positioned a sufficient distance from the patient's skin in order to deliver a substantially uniform dose of light. It can also be appreciated that the light source of the present invention is capable of decreasing hot spots on the surface of a patient's skin to provide a safer delivery to the patient. Also, a substantially uniform dose of light across the surface of the device ensures that all of the tissue is effectively treated with the same therapeutically effective dose.

The ultrasonic transducer of the present invention produces ultrasound with an intensity that is substantially constant across the surface of the device so as to provide a substantially uniform ultrasound field. In one aspect, the ultrasonic transducer has a beam non-uniformity ratio (BNR) (i.e., the ratio between peak intensity and average intensity in the beam) of 3 or lower (e.g., about 3, 2.8, 2.6, 2.4, 2.2, 2, 1.8, 1.6, 1.4, 1.2, 1 or lower). As described in more detail below, the ultrasonic transducer may comprise, for example, a flexible piezoelectric coating (film or paint). It can be appreciated that the ultrasonic transducer is capable of decreasing hot spots on the surface of a patient's skin to provide a safer delivery to the patient. Also, a substantially uniform dose of ultrasound across the surface of the device ensures that all of the tissue is effectively treated with the same therapeutically effective dose.

Figure 2:
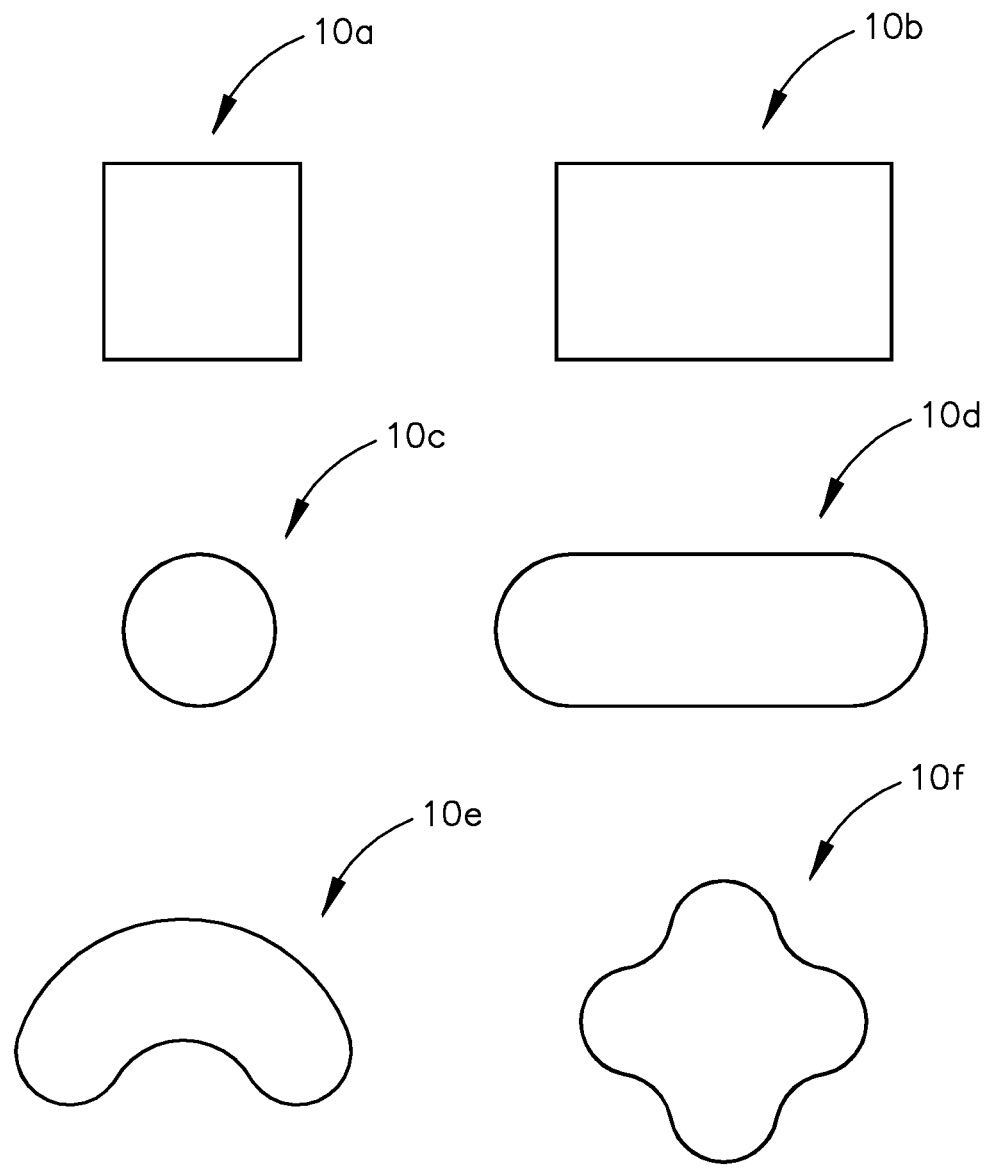
FIG. 2 is a top plan view of various exemplary shapes for the device of the present invention.

The device may be in the form of a patch, pad, mask, wrap, fiber, bandage or cylinder, for example. The device may have a variety of shapes and sizes. For example, the device may be square, rectangular, circular, elliptical, clover-shaped, oblong, or crescent/moon-shaped, such as the devices 10a-10f generally illustrated in FIG. 2. The overall surface area of one side of the device may range from, for example, 1 cm² to 1 m², although typically the surface area is about 1 to 2000 cm² (e.g., about 1, 4, 9, 16, 25, 36, 49, 64, 81, 100, 121, 144, 169, 196, 225, 289, 324, 361, 400, 441, 484, 529, 576, 625, 676, 729, 784, 841, 900, 961, 1024, 1089, 1156, 122, 1296, 1369, 1444, 1521, 1600, 1681, 1764, 1849, 1936 or 2000 cm² or some range therebetween). The device is thus well adapted to be applied to various areas of the patient's body, for example, the face, eyelids, eyebrows, forehead, lips, mouth, nose, ears, neck as well as the arms, legs, hands, fingers, feet, toes, stomach, and the like.

The total thickness of the device is preferably about 1 cm or less (e.g., about 1, 0.9, 0.8, 0.7, 0.6, 0.5, 0.4, 0.3, 0.2, 0.1 cm or less). Most preferably, the total thickness of the device is about 5 mm or less (e.g., about 5, 4.8, 4.6, 4.4, 4.2, 4, 3.8, 3.6, 3.4, 3.2, 3 mm or less).

In one aspect, the device is substantially planar in its form, although it is preferably flexible and/or conformable. The device is preferably flexible and is more preferably conformable such that it may conform to the contours of the body.

In another aspect, the device is applied to the skin surface for various therapies and cosmetic applications. The device may be used in conjunction with a therapeutic and/or cosmetic composition to be applied to the skin, including gel pads (such as hydrogel pads), lotions, gels, creams, ointments, foams, roll-on formulations, mousses, aerosol and non-aerosol sprays.

The device may be manufactured by known methods including, for example, spin coating, knife coating, spin casting, drop casting, vapor deposition or sputtering, crystalline growth, patterned etching, dip coating, or by printing techniques such as screen printing, flexographic printing, intaglio printing, ink jet printing, 3D printing, off-setting, transfer processes, or by spray applications.

For purposes of description herein, it is to be understood that the invention may assume various alternative configurations, orientations and step sequences, except where expressly specified to the contrary. It is also to be understood that the specific devices and processes described herein and illustrated in the attached drawings are exemplary embodiments of the present invention. Hence, specific dimensions and other physical characteristics relating to the embodiments disclosed herein are not to be considered as limiting.

As used herein, the singular forms "a," "an" and "the" include plural reference unless the context clearly dictates otherwise. Thus, for example, reference to a "layer" includes aspects having two or more such layers unless the context clearly indicates otherwise.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third. As will also be understood by one skilled in the art, all language such as "up to," "at least," and the like include the number recited and refer to ranges which can be subsequently broken down into subranges as discussed above. Finally, as will be understood by one skilled in the art, a range includes each individual member. Thus, for example, reference to 1-3 layers refers to groups having 1, 2, or 3 layers.

As used herein, the terms "optional" or "optionally" mean that the subsequently described component or element may or may not be present, and that the description includes instances where said component or element is present and instances where it is not.

The various elements/layers of the device of the present invention will now be described in more detail.

Substrate

In some exemplary embodiments, the device of the present invention comprises a device substrate. The substrate may be any substance capable of supporting the various layers/films of the device. The device substrate is preferably flexible and/or conformable to a surface in which the device will be used (e.g., the contours of a patient's body). The device substrate can comprise, for example, an inorganic material, an organic material, or a combination of inorganic and organic materials. The device substrate may be, for example, made from metals, plastics or glass. The device substrate may be any shape to support the other components of the device, for example, the device substrate may be substantially flat or planar, curved, or have portions that are substantially flat portions and curved portions. Most preferably, the device substrate is transparent, flexible, and conformable in nature. Ideally, the material is a latex-free, non-toxic, non-allergenic material, which is resistant to UV, sunlight and most infection control products.

In exemplary embodiments, the substrate may be comprised of a silicon-based material, rubber, thermoplastic elastomers (TTP), or other polymeric material, such as polyester, polyethylene terephthalate (PET), polyethylene naphthalate (PEN), polycarbonate, polystyrene, polyacryl, polyether sulfone (PES), etc. Transparent substrates may include, for example, polyethylene, ethylene-vinyl acetate copolymers, polyimide (PI), polyetherimide (PEI), ethylene-vinyl alcohol copolymers, polypropylene, polystyrene, polymethyl methacrylate, PVC, polyvinyl alcohol, polyvinylbutyral, polyether ether ketone, polysulfone, polyether sulfone, as well as fluoropolymers, such as, fluorinated ethylene-propylene (FEP), tetrafluoroethylene-perfluoroalkyl vinyl ether copolymers, polyvinyl fluoride, tetrafluoroethylene-ethylene copolymers, tetrafluoroethylene-hexafluoropropylene copolymers, polychlorotrifluoroethylene, polyvinylidene fluoride, polyester, polycarbonate, polyurethanes, polyimide or polyether imide.

In another exemplary embodiment, the transparent substrate is a polyester film, such as Mylar. In another aspect, the substrate comprises a polyetheretherketone film commercially available from Victrex under the name APTIV. In still another aspect, the substrate is a thin film sold under the name Flexent by Konica Minolta or flexible glass such as Willow Glass by Dow Corning. Ideally, substrates in direct or indirect contact with organic layers will have exceptional barrier capabilities that withstand heat, offer flexibility, have sustained reliability and can be mass produced.

Conductive Layers (Electrodes)

The device of the present invention comprises a plurality of conductive layers (i.e., electrodes), namely, a cathode and an anode for the light source and/or a cathode and an anode for the ultrasonic transducer. The cathode or anode may comprise a shared electrode such that the same conductive layer serves as a common cathode or as a common anode for both the light source and the ultrasonic transducer. In an exemplary embodiment, the light source and ultrasonic transducer each have an anode and share a common cathode. In this embodiment, the anode for the light source comprises, for example, a transparent conductive oxide (TCO), such as, but not limited to, indium tin oxide (ITO), zinc oxide (ZnO), and the like. The anode for the ultrasonic transducer and the common cathode each comprise, for example, a thin metal film such as aluminum, copper, gold, molybdenum, iridium, magnesium, silver, lithium fluoride and alloys thereof, or a non-metal conductive layer.

Because the light source must emit light through one or more electrodes, at least one of the electrodes is transparent. The transparent electrode is positioned on the side of the light source designed to be facing the skin. For a device intended to emit light only through the bottom electrode (i.e., skin-facing electrode), the top electrode (i.e., electrode facing away from the skin) does not need to be transparent. The top electrode may thus comprise an opaque or light-reflective metal layer having a high electrical conductivity. Where a top electrode does not need to be transparent, using a thicker layer may provide better conductivity, and using a reflective electrode may increase the amount of light emitted through the transparent electrode by reflecting light back towards the transparent electrode. Fully transparent light sources may also be fabricated, where both electrodes are transparent.

The thickness of each electrode is typically about 200 nm or less (e.g., about 200, 180, 160, 140, 120, 100, 90, 80, 70, 60, 50, 40, 30 nm or less). Preferably, the thickness of each electrode is less than 10 nm (e.g., about 10, 9, 8, 7, 6, 5, 4, 3, 2, 1, 0.8, 0.6, 0.4, 0.2 nm or less or some range therebetween).

The electrodes are preferably flexible in nature. In exemplary embodiments, the conductive materials of one or more of the electrodes may include, but are not limited to, transparent conductive polymer materials, such as indium tin oxide (ITO), fluorine-doped tin oxide (FTO), $ZnO-Ga_2O_3$, $ZnO-Al_2O_3$, $SnO_2-Sb_2O_3$, and polythiophene. In addition, the electrodes may be comprised of silver or copper grids or bushbars plated on a transparent substrate or silver nanowires or nanoparticles deposited on a substrate with a poly(3,4-ethylenedioxythiophene) poly(styrenesulfonate) (PEDOT:PSS) coating. Additional conductive polymer layers may be added to improve conductivity.

In one aspect, the transparent conductive electrode may be carbon-based, for example, carbon nanotubes, carbon nanowires, or graphene, and the like. One preferred electrode (typically for infrared) comprises graphene. While one or two layers of graphene is preferred, the electrode may comprise about 1 to 20 layers of graphene (e.g., 1, 2, 3, 4, 5, 6, 7, 8, 9, 10, 11, 12, 13, 14, 15, 16, 17, 18, 19, 20 layers or some range therebetween). The graphene electrode(s) also have the effect of protecting the photoactive layer sandwiched between them from oxidation. Therefore, environmental stability of the device can be improved. The graphene electrode may optionally have a plurality of plasmonic nanostructures, which may have various morphologies (spherical, rods, discs, prisms, etc.). Exemplary nanostructures include those made of gold, silver, copper, nickel, and other transition metals, for example gold nanoparticles, silver nanoparticles, copper nanoparticles, nickel nanoparticles, and other transition metal nanoparticles. In general, any electrically conductive materials, such as oxides and nitrides, of surface plasmonic resonance frequencies in the visible spectrum can be made into plasmonic nanostructures for the same purpose. In exemplary embodiments, the plasmonic particles have the size of about 1 nm to about 300 nm (e.g., about 10, 50, 100, 150, 200, 250, 300 nm, or some range therebetween).

Light Source

In some exemplary embodiments, the device of the present invention includes a thin light source that may comprise, for example, OLEDs or printable LEDs (organic or inorganic). In general terms, the light source comprises a flexible light emitter located between two conductive layers (i.e., electrodes) comprising an anode and a cathode, wherein the flexible light emitter emits light in response to an electric current applied to the anode and cathode. One typical light source uses a transparent substrate, a transparent anode, a flexible light emitter, and a reflective cathode. Light generated from the flexible light emitter is emitted through the transparent anode and transparent substrate. This is commonly referred to as a bottom-emitting light source. Alternatively, the light source may include a substrate, a reflective anode, a flexible light emitter, a transparent cathode, and a transparent encapsulating cover. Light generated from the flexible light emitter is emitted through the transparent cathode and transparent encapsulating cover. This is commonly referred to as a top-emitting light source. The present invention includes light sources having both bottom-emitting and top-emitting configurations. Of course, one skilled in the art will appreciate that other types of light sources may also be used in accordance with the present invention.

As used herein, the term "transparent" generally means transparency for light and includes both clear transparency as well as translucency. Generally, a material is considered transparent if at least about 50%, preferably about 60%, more preferably about 70%, more preferably about 80% and still more preferably about 90% of the light illuminating the material can pass through the material. In contrast, the term "opaque" generally refers to a material in which the light is substantially absorbed or reflected, e.g., at least 90% of the light is absorbed or reflected, and typically at least 95% of the light is absorbed or reflected.

The total thickness of the light source is preferably about 3 mm or less (e.g., about 3, 2.8, 2.6, 2.4, 2.2, 2, 1.8, 1.6, 1.4, 1.2, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01 mm or less). The thickness of the flexible light emitter in the light source is preferably about 2 mm or less (e.g., about 2, 1.8, 1.6, 1.4, 1.2, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01 mm or less). Most preferably, the flexible light emitter is about 10 to 200 nm in thickness (e.g., about 200, 180, 160, 140, 120, 100, 90, 80, 70, 60, 50, 40, 30, 20, 10 nm, or some range therebetween).

OLEDs

As noted above, the light source of the present invention may comprise OLEDs in which the flexible light emitter is a thin organic film. As used herein, the term "organic" with respect to OLEDs encompasses polymeric materials as well as small molecule organic materials that may be used to fabricate organic opto-electronic devices. Such materials are well known in the art. "Small molecule" refers to any organic material that is not a polymer, and it will be appreciated that "small molecules" may actually be quite large. "Small molecules" may include repeat units in some circumstances. For example, using a long chain alkyl group as a substituent does not remove a molecule from the "small molecule" class. "Small molecules" may also be incorporated into polymers, for example as a pendent group on a polymer backbone or as a part of the backbone. "Small molecules" may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules. In general, a "small molecule" has a well-defined chemical formula with a single molecular weight, whereas a polymer has a chemical formula and a molecular weight that may vary from molecule to molecule.

Generally speaking, in the flexible light emitter, electrons and holes recombine to radiate photons. The radiative photon energy emitted from the flexible light emitter corresponds to the energy difference between the lowest unoccupied molecular orbital (LUMO) level and the highest occupied molecular orbital (HOMO) level of the organic material. Photons of lower energy/longer wavelength may be generated by higher-energy photons through fluorescent or phosphorescent processes.

As described below, the flexible light emitter may optionally include one or more of a hole injection material (HIM), a hole transport material (HTM), a hole blocking material (HBM), an electron injection material (EIM), an electron transport material (ETM), an electron blocking material (EBM), and/or an exciton blocking material (ExBM).

In one aspect, the emissive electroluminescent layer may include a hole injection material (HIM). A HIM refers to a material or unit capable of facilitating holes (i.e., positive charges) injected from an anode into an organic layer. Typically, a HIM has a HOMO level comparable to or higher than the work function of the anode, i.e., −5.3 eV or higher.

In another aspect, the emissive electroluminescent layer may include a hole transport material (HTM). A HTM is characterized in that it is a material or unit capable of transporting holes (i.e., positive charges) injected from a hole injecting material or an anode. A HTM has usually high HOMO, typically higher than −5.4 eV. In many cases, HIM can also function as HTM, depending on the adjacent layer.

In another aspect, the emissive electroluminescent layer may include a hole blocking material (HBM). A HBM generally refers to a material which, if deposited adjacent to an emitting layer or a hole transporting layer in a multilayer structure, prevents the holes from flowing through. Usually it has a lower HOMO as compared to the HOMO level of the HTM in the adjacent layer. Hole-blocking layers are frequently inserted between the light-emitting layer and the electron-transport layer.

In another aspect, the emissive electroluminescent layer may include an electron injection material (EIM). An EIM generally refers to a material capable of facilitating electrons (i.e., negative charges) injected from a cathode into an organic layer. The EIM usually has a LUMO level comparable to or lower than the working function of the cathode. Typically, the EIM has a LUMO lower than −2.6 eV.

In another aspect, the emissive electroluminescent layer may include an electron transport material (ETM). An ETM generally refers to a material capable of transporting electrons (i.e., negative charges) injected from an EIM or a cathode. The ETM has usually a low LUMO, typically lower than −2.7 eV. In many cases, an EIM can serve as an ETM as well, depending on the adjacent layer.

In another aspect, the emissive electroluminescent layer may include an electron blocking material (EBM). An EBM generally refers to a material which, if deposited adjacent to an emissive or electron transporting layer in a multilayer structure, prevents the electron from flowing through. Usually it has a higher LUMO as compared to the LUMO of the ETM in the adjacent layer.

In another aspect, the emissive electroluminescent layer may include an exciton blocking material (ExBM). An ExBM generally refers to a material which, if deposited adjacent to an emitting layer in a multilayer structure, prevents the excitons from diffusing through. ExBM should have either a higher triplet level or singlet level as compared to the emitting layer or other adjacent layer.

Exemplary OLED materials are described in Hammond et al., U.S. Published Patent Application No. 2010/0179469; Pan et al., U.S. Published Patent Application No. 2013/0006119; Buchholz et al., PCT Published Patent Application No. WO 2012/010238; and Adamovich et al., U.S. Published Patent Application No. 2007/0247061, all of which are incorporated herein by reference.

Figure 3A:
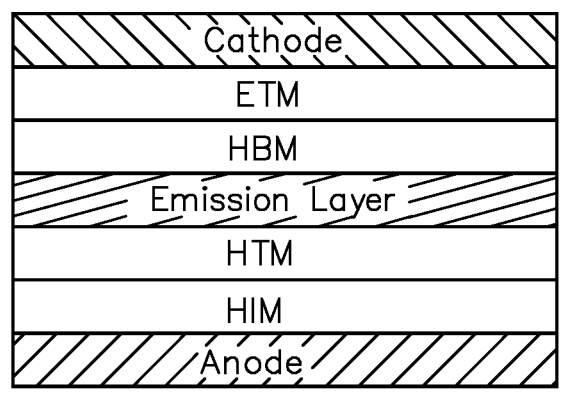
FIG. 3A illustrates an exemplary OLED structure for use in the device of the present invention.

Referring to FIG. 3A, a typical sequence of materials found in the flexible light emitter between the anode and the cathode of the OLED is HIM, HTM, emission layer, HBM, and ETM. Another typical sequence of materials is HTM, emission layer, and ETM. Of course, other sequences of materials are also possible and within the scope of the present invention. Further, the OLED may comprise one or more interlayers.

In one aspect, the flexible light emitter comprises a single layer. The flexible light emitter may comprise, for example, a conjugated polymer which is luminescent, a hole-transporting polymer doped with electron transport molecules and a luminescent material, or an inert polymer doped with hole transporting molecules and a luminescent material. The flexible light emitter may also comprise an amorphous film of luminescent small organic molecules which can be doped with other luminescent molecules.

In another aspect, the flexible light emitter may comprise one or more different emissive materials in either the same emission layer or in different emission layers. For example, the flexible light emitter may comprise 5, 4, 3, 2, or 1 radiation emitting materials. The various different emissive materials may be selected from the emissive materials described in the references set forth above, but any other suitable emissive material can be employed. If two emissive materials are used in one emission layer, the absorption spectrum of one of the two emissive materials preferably overlaps with the emission spectrum of the other emissive material. The emissive materials may be arranged in stacked layers or side-by-side configurations. The emissive layer may comprise a continuous region forming a single emitter or a plurality of light emitters. The plurality of light emitters may emit light with substantially different wavelengths. The plurality of light emitters may be vertically stacked within the emissive layer or they may form a mixture. In some embodiments, a dopant is dispersed within an organic host matrix. In one embodiment, a layer of quantum dots is sandwiched between two organic thin films.

In another aspect, the flexible light emitter may comprise a plurality of layers sharing a common anode and/or cathode. In this case, individual layers are stacked one on top of another. The stacked configuration may generally include intermediate electrodes disposed between adjacent layers such that successive layers share an intermediate electrode, i.e., a top electrode of one layer is the bottom electrode of another in the stack. The stacked layers may be formed of different materials, and therefore, different emissions spectra.

The OLEDs may produce light in the visible range (380 to 700 nm), the ultraviolet range (UVA: 315 to 400 nm; UVB: 280 to 315 nm; UVC: 100-280 nm), near infrared light (700 to 1500 nm) and/or far infrared light (about 1500 to 11,000 nm). Visible light corresponds to a wavelength range of approximately 380 to 700 nm and are usually described as a color range of violet through red. The human eye is not capable of seeing radiation with wavelengths outside this visible spectrum such as in the ultraviolet or infrared range. The visible spectrum from shortest to longest wavelength is generally described as violet to deep blue (approximately 400 to 450 nm), blue (approximately 450 to 490 nm), green (approximately 490 to 560 nm), yellow (approximately 560 to 590 nm), orange (approximately 590 to 630 nm), and red (approximately 630 to 700 nm). Ultraviolet radiation has a shorter wavelength than the visible violet light and infrared radiation has a longer wavelength than visible red light. The emission spectrum may be one selected from a NIR, UV, white, a red, a green, a blue, a yellow, an orange, a cyan, or a magenta spectrum or a combination thereof. Selection of wavelengths for therapeutic and/or cosmetic purposes may be made by selecting the appropriate materials and layers so that the same device may provide multiple or combined wavelengths. By appropriately mixing different materials and layers, the output spectrum may also be visually substantially white. The broadband spectra of individual layers may be mixed to form an output spectrum which may be very close to naturally white light to human eyes or as needed for the therapeutic and/or cosmetic effect.

There are multiple methods of producing white light using emissive layers in the device of the present invention. One method is to use individual emissive layers that emit visible light in the red range, the green range, and the blue range. The emissive layers may be in a single layer or in a layered structure. Another method involves the use of a phosphor material capable of converting monochromatic light from blue or UV to broad-spectrum white light or by converting just a portion of the blue light with a yellow emitting phosphor material.

In one aspect, the device emits a relatively broad band spectrum such that the full width at half maximum (FWHM) of the individual spectrum may be larger than 50 nm, 100 nm, 150 nm, or even larger than 200 nm. In another aspect, the device may produce a narrow band spectrum with a FWHM less than about 50 nm. This may be advantageous in certain phototherapy applications where the tissue or photosensitizing medication responds to a narrow wavelength range.

The flexible light emitter may be substantially transparent. When mostly transparent layers are used, a plurality of emissive layers may be vertically stacked without substantially blocking light emission from individual layers. The flexible light emitter may comprise a single or multiple layers, for example, a combination of p- and n-type materials. The p- and n-type materials may be bonded to each other in the layer. The bonding may be ionic or covalent bonding, for example. The multiple layers of the flexible light emitter may form heterostructures therebetween.

Printable LEDs

As noted above, the light source of the present invention may comprise printable LEDs (organic or inorganic). There are several known methods for printing such LEDs, as described below.

In one method, the light source comprises a plurality of individual LEDs suspended and dispersed in a liquid or gel comprising one or more solvents and a viscosity modifier so as to form a diode ink that is capable of being printed on a flexible substrate (e.g., through screen printing, flexographic printing and the like). In one aspect, the average surface area concentration of LEDs is from about 25 to 50,000 LEDs per square centimeter. In general, each LED includes a light emitting region, a first metal terminal located on a first side of the light emitting region, and a second metal terminal located on a second side of the light emitting region. The first and second metal terminals of each LED may be electrically coupled to conductive layers (i.e., electrodes) to enable the light emitting region to emit light when energized.

Figure 3B:
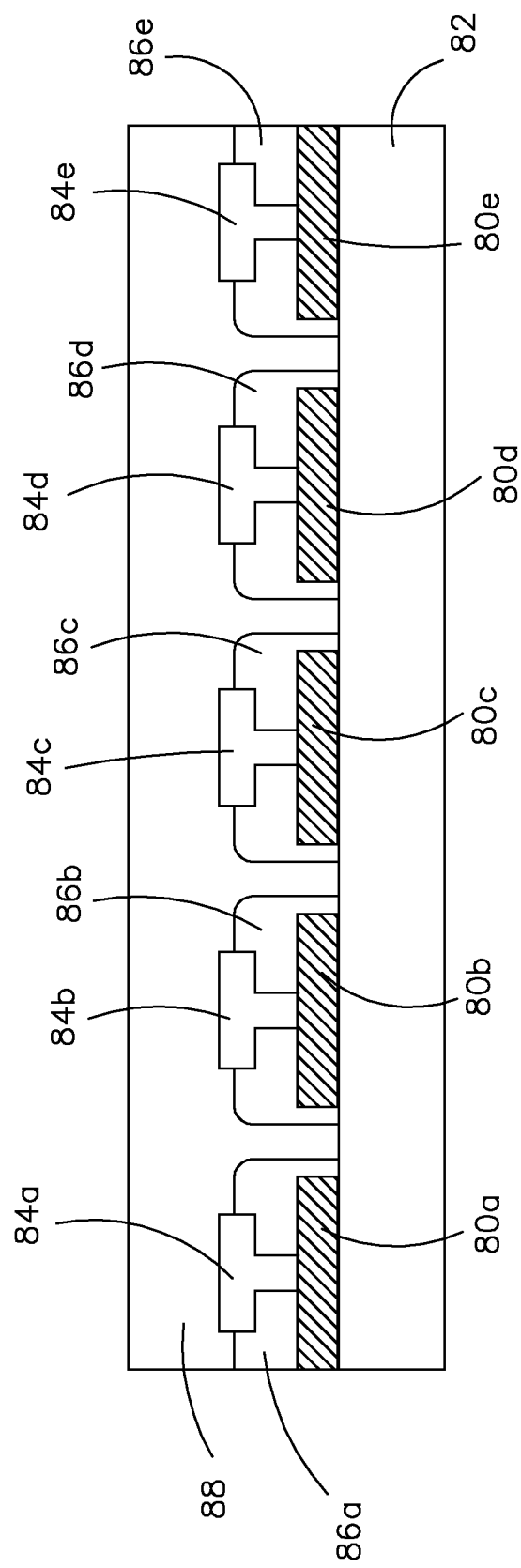
FIG. 3B illustrates an exemplary printable LED structure for use in the device of the present invention.

An exemplary light source is shown generally in FIG. 3B, wherein only five LEDs are provided in order to simplify the description. As can be seen, this light source includes a plurality of conductors 80a-80e deposited on a flexible substrate 82. A plurality of LEDs 84a-84e are deposited on the conductors 80a-80e such that the first metal terminals of the LEDs 84a-84e are electrically coupled to the conductors 80a-80e. One skilled in the art will appreciate that the LEDs 84a-84e may be formed of various shapes. Preferably, the LEDs 84a-84e settle into a position over conductors 80a-80e such that they maintain their polarity based on the shape of the LEDs. Next, a plurality of dielectric layers 86a-86e are deposited over the LEDs 84a-84e and the conductors 80a-80e, as shown. Another conductor 88 is then deposited over the LEDs 84a-84e and dielectric layers 86a-86e such that the second metal terminals of the LEDs 84a-84e are coupled to the conductor 88. One skilled in the art will appreciate that the substrate 82 and conductors 80a-80e may be transparent so that light is emitted from the bottom of the device and/or conductor 82 may be transparent so that light is emitted from the top of the device.

Various configurations of printable LEDs that may be manufactured in accordance with the above method are described in Lowenthal et al., U.S. Pat. No. 8,415,879, which is incorporated herein by reference.

In another method, the light source comprises LEDs that are created through a printing process. In this method, a substrate is provided that includes a plurality of spaced-apart channels. A plurality of first conductors are formed on the substrate such that each first conductor is positioned in one of the channels. Next, a plurality of substantially spherical substrate particles are coupled to the first conductors and, then the substantially spherical substrate particles are converted into a plurality of substantially spherical diodes. The substantially spherical diodes may comprise, for example, semiconductor LEDs, organic LEDs encapsulated organic LEDs, or polymer LEDs. A plurality of second conductors are then formed on the substantially spherical diodes. Finally, a plurality of substantially spherical lenses suspended in a polymer (wherein the lenses and suspending polymer have different indices of refraction) are deposited over the substantially spherical diodes and the second conductors. Thus, in this method, the LED's are built up on the substrate as opposed to being mounted on the substrate. Various configurations of printable LEDs that may be manufactured in accordance with the above method are described in Ray et al., U.S. Pat. No. 8,384,630, which is incorporated herein by reference.

Micro-Lens Array

In the present invention, the device may optionally include a light dispersion layer, such as a micro-lens array. It has been found that one of the key factors that limits the efficiency of OLED devices is the inefficiency in extracting the photons generated by the electron-hole recombination out of the OLED devices. Due to the high optical indices of the organic materials used, most of the photons generated by the recombination process are actually trapped in the devices due to total internal reflection. These trapped photons never leave the OLED devices and make no contribution to the light output from these devices. In order to improve the extraction or out-coupling of light from OLEDs, the device may include an internal scattering layer of high index particles such as TiOx in a transparent photoresist or a micro-lens array (MLA) layer. Exemplary MLAs and methods for forming the same are described in Gardner et al., U.S. Published Patent Application No. 2004/01217702; Chari et al. U.S. Pat. No. 7,777,416; Xu et al., U.S. Pat. No. 8,373,341; Yamae et al., *High-Efficiency White OLEDs with Built-up Outcoupling Substrate*, SID Symposium Digest of Technical Papers, 43 694 (2012); and Komoda et al., *High Efficiency Light OLEDS for Lighting*, J. Photopolymer Science and Technology, Vol. 25, No. 3 321-326 (2012).

Ultrasonic Transducer

In some exemplary embodiment, the device of the present invention comprises an ultrasonic transducer for producing ultrasound. In one aspect, the device produces low frequency ultrasound. In another aspect, the device produces high frequency ultrasound. In still another aspect, the device produces both low frequency ultrasound and high frequency ultrasound (i.e., a dual frequency ultrasound device) and may have either a unimorph design or a bimorph design, as discussed below. The low and high frequency ultrasound can be applied simultaneously, sequentially or separately, e.g., sequentially as several alternating single applications of low and high frequency ultrasound or separately where a series of applications of low frequency ultrasound is alternated with a series of applications of high frequency ultrasound.

"Ultrasound" as used herein includes near ultrasound and generally refers to sound at a frequency of greater than about 2 kHz up to about 20 MHz or more (e.g., 2, 5, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10,000, 11,000, 12,000, 13,000, 14,000, 15,000, 16,000, 17,000, 18,000, 19,000, 20,000 kHz, or some range therebetween). As used herein, "low frequency ultrasound" includes near ultrasound and generally has a frequency in the range of about 2 kHz to 500 kHz (e.g., about 2, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500 kHz or some range therebetween). Preferred low frequency ultrasound ranges are about 2 kHz to 200 kHz, 15 kHz to 150 KHz, 15 kHz to 100 kHz, 35 kHz to 100 kHz, and more preferably about 50 kHz to 100 kHz. As used herein, "high frequency ultrasound" includes ultrasound generally having a frequency in the range of about 500 kHz to 20 MHz or more (e.g., about 500, 600, 700, 800, 900, 1000, 2000, 3000, 4000, 5000, 6000, 7000, 8000, 9000, 10,000, 11,000, 12,000, 13,000, 14,000, 15,000, 16,000, 17,000, 18,000, 19,000, 20,000 kHz or some range therebetween). Preferred high frequency ultrasound ranges are about 0.5 to 15 MHz, 0.5 to 10 MHz, 0.5 MHz to 5 MHz, 0.5 MHz to 3.5 MHz, 1 MHz to 5 MHz, 1 MHz to 3.5 MHz, 1.5 MHz to 3.5 MHz, and 1 to 3 MHz.

In one aspect, the device produces low frequency ultrasound (preferably about 2 kHz to 200 kHz, even more preferably about 35 kHz to 100 kHz, and still more preferably about 50 to 100 kHz) and high frequency ultrasound (preferably about 0.5 MHz to 5 MHz, more preferably about 0.5 MHz to 3.5 MHz, even more preferably about 1 to 3 MHz). The high or low frequency ultrasound may be provided in continuous or pulsed modes modulated at frequencies of 0.1 Hz to 5 kHz, preferably in the range of about 10 to 1000 Hz (e.g., 10, 50, 100, 200, 300, 400, 500, 600, 700, 800, 900, 1000 Hz or some range therebetween at various duty factors, preferably in the range of 5-50% (e.g., about 5, 10, 15, 20, 25, 30, 35, 40, 45, 50% or some range therebetween), typically in the range of 10% to 20%.

In the present invention, the ultrasonic transducer in its simplest form comprises a thin, flexible ultrasound emitter (e.g., a piezoelectric coating (film or paint) or piezoceramic material) sandwiched between a pair of thin conductive electrodes. It will be appreciated that the electrodes for the flexible ultrasound emitter need not be transparent. Further, it will be appreciated that, in some embodiments, the cathode of the light source may also function as the cathode of the ultrasonic transducer. The ultrasonic transducer may operate at a variety of frequencies, including low and/or high frequencies.

The thickness of the flexible ultrasound emitter is a function of the frequency of the sound waves. Preferred thicknesses for the flexible ultrasound emitter (e.g., a piezoelectric coating (film or paint)) are about 50 to 200 μm (e.g., about 50, 60, 70, 80, 90, 100, 110, 120, 130, 140, 150, 160, 170, 180, 190, 200 μm, or some range therebetween). In other embodiments, the flexible ultrasound emitter (e.g., a piezoceramic material) may have a thickness of about 3 mm or less (e.g., about 3, 2.8, 2.6, 2.4, 2.2, 2, 1.8, 1.6, 1.4, 1.2, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01 mm or less).

In one embodiment, the device generates low frequency ultrasound. The device may generate low frequency ultrasound in at least three ways.

First, the device may include an ultrasonic transducer capable of generating ultrasound having a frequency of about 2 kHz to 500 kHz, preferably about 2 kHz to 200 kHz.

Second, the device may include an ultrasonic transducer capable of generating ultrasound at a frequency of about 100 kHz to 20 MHz (e.g., about 100, 200, 300, 400, 500, 600, 700, 800, 900, 1000, 1500, 2000, 2500, 3000, 3500, 4500, 5000, 6000, 7000, 8000, 9000, 10,000, 11,000, 12,000, 13,000, 14,000, 15,000, 16,000, 17,000, 18,000, 19,000, 20,000 kHz or some range therebetween) modulated at a frequency of about 2 kHz to 500 kHz, preferably about 2 kHz to 200 kHz. That is, the ultrasound signal is "on/off" at a frequency of 2 kHz to 500 kHz, preferably about 20 kHz to 200 kHz.

Third, the device may include an ultrasonic transducer capable of generating vibrational energy at a frequency of about 10 Hz to 1000 Hz (e.g., about 10, 20, 30, 40, 50, 60, 70, 80, 90, 100, 150, 200, 300, 400, 500, 600, 700, 800, 900, 1000 Hz or some range therebetween) modulated at a frequency of about 2 kHz to 500 kHz, preferably about 2 kHz to 200 kHz. That is, the vibrational energy produced by the transducer is "on/off" at a frequency of 2 kHz to 500 kHz, preferably about 2 kHz to 200 kHz. In one embodiment, the device produces vibration of about 10 Hz to 1000 Hz, preferably about 10 Hz to 100 Hz, more preferably about 10 Hz to 50 Hz, and most preferably about 15 Hz to 30 Hz, which is felt on the transducer surface, and can be tuned using pulse modulated currents to optimize higher frequency harmonics in the range of about 15 kHz to 100 kHz, more preferably about 15 kHz to 50 kHz, and most preferably about 15 kHz to 35 kHz.

The intensity of the low frequency ultrasound is preferably in the range of between about 0 and 3.0 W/cm$^2$ (e.g., about 5, 50, 100, 150, 200, 250, 300, 350, 400, 450, 500, 1000, 1500, 2000, 2500, 3000 mW/cm2 or some range therebetween), more typically between about 5 mW/cm$^2$ and 200 mW/cm$^2$. Exposures to the treatment site are typically for a period of between about 1 and 15 minutes (e.g., about 1, 2, 3, 4, 5, 6, 7, 8, 9, 10, 11, 12, 13, 14, or 15 minutes), but may be shorter or longer and/or pulsed. Other ultrasonic transducer parameters including, but not limited to, amplitude, duty cycle, distance from the treatment site, and application time may be varied to achieve sufficient enhancement of transdermal transport. The pressure amplitude may be varied from above about 0 to 50 kPa. The duty cycle can vary from between about 1% and 100%. The displacement may vary from about 25 picometers to several hundred nanometers.

The ultrasonic transducer may be made of any suitable ultrasound transducer material, such as a flexible piezoelectric coating (film or paint), a ceramic transducer, or a polymer block transducer. The transducer may be comprised of quartz, polyvinylidene fluoride (PVDF), ceramic including PZT and screen printed ceramic, magnetostrictive, or composite material including molded ceramic and benders. For example, the piezoelectric material may be selected from the group consisting of PZT, PVDF, lead zirconate titanate Pb(Zr,Ti)O3, lead metaniobate Pb(Nb2O6), modified lead titanate PbTi3, (Pb,Ca)TiO3, (Pb,Sm)TiO3, barium titanate BaTiO3, PMN-PT(1−x)Pb(Mg⅓,Nb⅔)O3−xPbTiO3, PZN-PT/BT Pb(ZN⅓,Nb⅔)O3−x Pb TiO3-BaTiO3, (1−x)Pb(ZN⅓,Nb⅔)O3−x(yPbTiO3-(1−y)PbZrO3).

In a preferred aspect, the transducer is comprised of a flexible piezoelectric coating (film or paint), such as PVDF or a co-polymer thereof. It will be appreciated to those skilled in the art that recent developments in flexible piezoelectric coatings, such as the PiezoPaint™ material available from Meggitt PLC, provide a piezoelectric material that can be applied on a variety of substrates. For example, the PiezoPaint™ PP-50B material is flexible, printable (e.g., using screen-printing, pad-printing or stencil printing techniques), exhibits relatively high sensitivity ($d_{33}$ coefficient up to 45 pC/N), and may be processed at extremely low temperatures (less than 150° C.). Of course, other flexible piezoelectric coatings may also be used in the device of the present invention.

As noted above, the device may generate both low frequency ultrasound and high frequency ultrasound (i.e., a dual frequency ultrasound device) and may have either a unimorph design or a bimorph design.

With a unimorph design, a single ultrasound emitter is used to deliver low frequency ultrasound in the range of 2 kHz to 500 kHz and high frequency ultrasound in the range of 500 kHz to 20 MHz. In one aspect, the ultrasound emitter comprises a flexible piezoelectric coating (e.g., PiezoPaint™ material by Meggitt PLC) that is able to operate at both low and high frequencies (i.e., a broadband device).

In one embodiment, the ultrasound emitter is bonded to an elastic substrate (e.g., a metal substrate) in such a manner as to generate both low and high frequency ultrasound. In this case, the device is designed to use the lateral resonance of the ultrasound emitter in combination with the substrate so as to optimize low frequency resonance and provide a low frequency mechanical bending resonance mode, while also enabling the thickness resonance mode to provide high frequency operation. As such, the ultrasound emitter has a low frequency mechanical bending resonance mode when the ultrasound emitter is excited, in use, by a voltage which includes a low frequency oscillating component, and also has a relatively high frequency thickness resonance mode when the ultrasound emitter is excited, in use, by a voltage which includes a relatively high frequency oscillating component. An example of such a device is described in Galluzzo et al., U.S. Published Patent Application No. 2012/0267986, which is incorporated by reference in its entirety. In this embodiment, the substrate may function as the cathode (or anode) for the ultrasonic transducer, as well as a common cathode for the light source.

Alternatively, the ultrasound emitter operates in a conventional lateral resonance mode to deliver lower frequency ultrasound and a thickness resonance mode to deliver higher frequency ultrasound. In this case, the ultrasound emitter is not bonded to a substrate as described above. Such a design is not preferred insofar as the range of frequencies produced between the lateral resonance mode and the thickness resonance mode are limited to a ratio of about 6:1. As such, the device would not, for example, be able to provide low frequency ultrasound at 50 kHz and high frequency ultrasound at 3 MHz. With that said, such an ultrasound emitter could be used as either a low frequency transducer or a high frequency transducer whereby the additional operating frequency provides a therapeutic effect.

With a bimorph design, two different ultrasound emitters are used to deliver low frequency ultrasound in the range of 2 kHz to 500 kHz and high frequency ultrasound in the range of 500 kHz to 20 MHz. In a preferred embodiment, each of the low and high frequency ultrasound emitters comprises a flexible piezoelectric coating (e.g., PiezoPaint™ material by Meggitt PLC), wherein one ultrasound emitter is driven at a low frequency and the other ultrasound emitter is driven at a high frequency. These materials are able to deliver ultrasound in a wide range of frequencies, e.g., low frequency ultrasound at 50 kHz and high frequency ultrasound at 3 MHz. An example of such a device is described in Luebecke, U.S. Published Patent Application No. 2008/0051580, which is incorporated by reference in its entirety.

Low frequency ultrasound is believed to be useful to facilitate delivery of molecules through the skin (a process termed "sonophoresis"). The low frequency ultrasonic energy provides cavitational effects in the skin, which improves drug delivery into and through the skin. In particular, the application of low frequency ultrasound (e.g., about 2 kHz to 200 kHz) dramatically enhances transdermal transport of drugs. Cavitation may cause disordering of the stratum corneum lipids. In addition, oscillations of cavitation bubbles may result in significant water penetration into the disordered lipid regions. This may cause the formation of aqueous channels through the intercellular lipids of the stratum corneum. This allows permeants to transport across the disordered lipid domains, then across keratinocytes and the entire stratum corneum. This transport pathway may result in an enhanced transdermal transport as compared to passive transport because the diffusion coefficients of permeants through water, which is likely to primarily occupy the channels generated by ultrasound, are up to 1000-fold higher than those through the ordered lipid bilayers, and the transport path length of these aqueous channels may be much shorter (e.g., by a factor of up to about 25) than that through the tortuous intercellular lipids in the case of passive transport.

High frequency ultrasound has a lesser sonophoretic effect than low frequency, although it is capable of sonophoresing small molecules (typically less than about 500 daltons). However, high frequency ultrasound has many other effects beneficial to the skin in that it stimulates fibroblast proliferation, stimulates collagen and other extracellular matrix (ECM) component formation (e.g., fibrillin), stimulates blood supply, renews the elastic quality of ECM which stiffen with age, stimulates the expression of Heat Shock Proteins (HSPs—intracellular molecular chaperones) in fibroblasts (dermis) and keratinocytes (epidermis) through thermal and mechanical stimulation.

Other ultrasound parameters that may be readily determined by those skilled in the art include, but are not limited to, amplitude, duty cycle, distance from the skin, coupling agent composition, and application time, which may be varied to achieve sufficient enhancement of transdermal transport and therapeutic dose.

Matching Layer

The device of the present invention may optionally include an acoustic impedance matching layer. The matching layer is typically located between the skin-facing surface of the device and the ultrasonic transducer. Most preferably, the matching layer is transparent, flexible and/or conformable in nature. Ideally the material is latex-free, non-toxic, non-allergenic material, which is resistant to UV, sunlight and most infection control products.

It will also be appreciated that the device may include multiple matching layers, as desired. When an acoustic wave encounters a boundary between two layers having a relatively large variance in their respective acoustic impedances, the acoustic wave is reflected at the boundary. Using a plurality of matching layers enables the acoustic impedance of each layer to be varied gradually to minimize reflections. It will also be appreciated that the larger the difference in the acoustic impedances of the therapeutic and/or cosmetic composition and the transducer, more matching layers may be employed to minimize reflections.

In one embodiment, the acoustic impedance of the therapeutic and/or cosmetic composition is matched closely enough to the acoustic impedance of the skin boundary, such that reflections at the skin layer boundary are minimized. As noted above, it is desirable to have some of the acoustic energy pass through the skin layer boundary into the tissue to provide a cavitation or therapeutic effect. The matching layer(s) thus direct the ultrasound acoustic energy from the transducer to the therapeutic and/or cosmetic composition, and the therapeutic and/or cosmetic composition may also act as a matching layer to direct some of the ultrasound into the upper layers of the dermal or epidermal tissue.

In exemplary embodiments, the matching layer may be comprised of a silicon-based material, rubber, thermoplastic elastomers (TTP), or other polymeric material, such as polyester, polyethylene terephthalate (PET), polyethylene naphthalate (PEN), polycarbonate, polystyrene, polyacryl, polyether sulfone (PES), etc. Transparent matching layers may include, for example, polyethylene, ethylene-vinyl acetate copolymers, polyimide (PI), polyetherimide (PEI), ethylene-vinyl alcohol copolymers, polypropylene, polystyrene, polymethyl methacrylate, PVC, polyvinyl alcohol, polyvinylbutyral, polyether ether ketone, polysulfone, polyether sulfone, as well as fluoropolymers, such as, fluorinated ethylene-propylene (FEP), tetrafluoroethylene-perfluoroalkyl vinyl ether copolymers, polyvinyl fluoride, tetrafluoroethylene-ethylene copolymers, tetrafluoroethylene-hexafluoropropylene copolymers, polychlorotrifluoroethylene, polyvinylidene fluoride, polyester, polycarbonate, polyurethanes, polyimide, and thermosets such as epoxies. Because the acoustic impedance of many polymeric materials is less than the preferred range, it may be necessary to increase the acoustic impedance by incorporating a filler such as PZT, tungsten, silica glass, titanium, tungsten carbide and glass powder. Typically, a particle size of 0.5 to 5 microns is used, and a filler in the range of 5 to 30% by volume is used although other percentages may be appropriate based on the material and particle size.

In another exemplary embodiment, the matching layer is a polyester film, such as Mylar. In another aspect, the substrate serves as the matching layer and comprises a polyetheretherketone film commercially available from Victrex under the name APTIV. In still another aspect, the matching layer is a thin film sold under the name Flexent by Konica Minolta or flexible glass such as Willow Glass by Dow Corning.

Transparent Heater Layer

The device of the present invention may also include an optional heater layer, which is preferably transparent, flexible and/or conformable. In one embodiment, the flexible transparent heater layer is formed adjacent the matching layer(s). Alternatively, the flexible transparent heater layer may be a part of the matching layer(s). For example, graphene may be incorporated into a polyethylene terephthalate (PET) film which is imbedded in or bonded to the matching layer to form a flexible transparent heater layer. The heater layer provides an even heating across the surface due to the printing or deposition of the heater layer. This is of importance in reducing hot spots and providing even heating over the tissue surface. Exemplary materials and methods for forming the flexible transparent heater layer are described in Kang et al., High-performance graphene-based transparent flexible heaters, Nano Lett 11 (12):5154-8 (2011); Sui et al., Flexible and Transparent Electrothermal Film Heaters Based on Graphene Materials, Small, Vol. 7, Issue 22, 3186-3192 (Nov. 18, 2011). The flexible transparent heater layer may be driven by AC, DC, or pulsed DC. Typically, low voltages and currents are needed to increase the tissue temperature from about 1 to 4° C. using resistive heating elements.

In one aspect, the device of the present invention is well adapted to provide light energy, ultrasound, and mild heating of about 1 to 2° C. (e.g., via light energy from the light source, ultrasound from the ultrasonic transducer, and heat from the flexible transparent heater layer, or combinations thereof). It is theorized that low frequency ultrasound causes cavitational effects which assist in the movement of therapeutic and/or cosmetic agents, such as those containing ascorbic acid, through the skin. Among other things, the light energy triggers the collagen regeneration and production by activation of fibroblasts. Heating the skin further assists in increasing transdermal permeability and increases microvascular perfusion, providing nutrients to the dermal and epidermal layers of the skin and underlying tissue.

In another aspect, the device of the present invention is well adapted to provide light energy, ultrasound, and mild heating of about 2 to 4° C. (e.g., via light energy from the light source, ultrasound from the ultrasonic transducer, and heat from the flexible transparent heater layer, or combinations thereof). It is theorized that low frequency ultrasound causes cavitational effects which assist in the movement of therapeutic and/or cosmetic agents, such as those containing ascorbic acid, through the skin. Among other things, the light energy triggers the collagen regeneration and production by activation of fibroblasts. The heating increases blood flow and assists in collagen remodeling. Heating of collagenous fibers also allows plastic deformation using heat-and-stretch to reform collagen and flatten out areas of tissue irregularities such as scar tissue, wrinkles and dermal lesions.

Electrical Stimulation Layer

The device of the present invention may include an optional electrical stimulation layer. The electrical stimulation layer is well suited to iontophoretically deliver a charged therapeutic and/or cosmetic agent to the skin, decrease muscle spasms or muscle hypertonicity, or improve muscle tone in case of muscle hypotonicity.

During iontophoresis, the current (which is typically DC or pulsed DC) is used to cause the therapeutic or cosmetic agent ions to move across the surface of the skin and diffuse into underlying tissue. To create an iontophoretic circuit, the positive and negative poles of the controllable waveform generator are electrically connected to positive and negative electrodes, respectively, applied to the skin of the patient. To iontophoretically deliver a positively charged medicament, the composition containing the medicament is coupled to the electrical stimulation layer in the device which is a positive electrode. A negative return electrode is applied to the surface of the skin at a separate location. On the other hand, to iontophoretically deliver a negatively charged medicament, the composition containing the medicament is coupled to an electrical stimulation layer in the device which is a negative electrode. A positive return electrode is applied to the surface of the skin at a separate location. Electrical current flows from the generator to the positive electrode and through the patient's skin to the negative electrode. The electromotive differential between the positive electrode and the negative electrode induces the negative polarity medicament to move as negative ions through the surface of the patient's skin in the direction of the positive electrode.

In another aspect, the return electrode is incorporated into the device itself. For example, one or more return electrodes may be positioned at the periphery of the surface of the device that is in contact with the skin, for example, adjacent to the matching layer of the device.

In one aspect, the electrical current is a DC current. In another aspect, the electrical current applied to the electrical stimulation layer comprises a DC current superimposed with either an AC current or a pulsed DC current. Preferably, the current ranges from about 1 to 10 mA (e.g., about 1, 2, 3, 4, 5, 6, 7, 8, 9, 10 mA, or some range therebetween) with about 2 to 4 mA being most preferred. The voltage is typically 100 V or less (e.g., about 100, 90, 80, 70, 60, 50 or 40 V or less). Typically, the treatment time is about 10 to 20 minutes such that the dosage per treatment time is about 40 to 80 mA*min (e.g., about 40, 50, 60, 70 or 80 mA*min).

In this embodiment, the therapeutic and/or cosmetic composition may include one or more therapeutic and/or cosmetic agents, such as those described herein. In one aspect, the therapeutic and/or cosmetic composition is incorporated into a gel or gel pad (such as a hydrogel or hydrogel gel pad) which is applied to the surface of the skin. The therapeutic and/or cosmetic composition may be incorporated into a membrane containing apparatus which controls the transport of molecules through the membrane with the exposure of ultrasound generated by the device, such as in Kost et al., U.S. Pat. No. 7,480,212. The conductive gel or gel pad may include, for example, a metal such as aluminum, carbon film or carbon film coated with a conductor such as silver, or silver chloride to reduce the potential for burns of the superficial tissue of the skin from the application of current. The therapeutic and/or cosmetic agent may comprise any conductive ionic molecule or compound that can be transdermally administered to a patient with an iontophoretic delivery system. Examples of common positive active agents include amine containing drugs, such as bupivacaine hydrochloride and lidocaine. Examples of common negative active agents include acidic drugs, such as ascorbic acid, acetic acid, salicylic acid, etc. Of course, the delivery of other active agents are also within the scope of the present invention.

The inclusion of an electrical stimulation layer in the device of the present invention permits electrical stimulation to be applied to the patient's skin. In one aspect, the device is capable of providing electroanethesia to the patient. In such a case, the devices are well suited for use in conjunction with a cosmetic procedure, such as laser resurfacing, fractal laser applications, plash phototherapy, ultrasound, light and surgeries using scalpels or other cutting or remodeling devices. Of course, other types of cosmetic procedures are also within the scope of the invention.

It will also be appreciated that the flexible transparent conductive layer (such as one containing graphene) may serve as the electrical stimulation layer. The graphene may be electrically coupled to a return electrode. Further, such a device can be used with a therapeutic and/or cosmetic composition which is conductive and typically ionic in nature. A return electrode is provided from the device on the body of the person undergoing treatment. Typically, a pulsed monophasic or DC current of the appropriate polarity is used to provide an iontophoretic effect to enhance ionic transport of the therapeutic and/or cosmetic composition through the skin. The composition also serves as an impedance matching layer between the conductive matching layer (containing the graphene) and the skin layer. Additional materials such as silver or silver chloride nanoparticles may also be coated on the electrode surface or included in the composition and/or hydrogel layer to buffer the iontophoretic composition. As an additional feature of the device of the present invention, a pulsed DC or AC current may be used in patterns that reduce muscle hypertonicity or reduce muscle disuse atrophy. These currents may be based on EMG firing patterns of agonist and antagonist muscles or sequences of stimulation which act in a similar way to voluntary exercise in the building of muscle strength, power and endurance. The on and off times, ramps, duty factors, waveforms, current levels and impedance requirements are well known in the art and are well established in this regard.

Ultrasonic Reflective Layer or Ultrasonic Absorptive Backing Layer

The device of the present invention may optionally include an ultrasonic reflective layer or ultrasonic absorptive backing layer. The ultrasonic reflective layer or ultrasonic absorptive backing layer is located between the surface of the device facing away from the skin and the ultrasonic transducer. The ultrasonic reflective layer is designed to prevent undesirable backward leakage of ultrasonic waves away from the patient. The ultrasonic reflective layer is typically a half-wavelength or quarter-wavelength reflector, which is made of high acoustic impedance materials, such as copper, other metals or ceramics. The ultrasonic reflective layer is preferably configured such that the phase relationship of the ultrasound is summative.

With some devices, it may not be desirable to have the ultrasound reflect back to the patient. Further, the reflection may provide a canceling phase which may reduce output. Thus, the device may include an ultrasonic absorptive backing layer. The absorptive backing layer is usually made of a material with acoustic impedance close to the piezoelectric resonator and having a very high damping coefficient. Because the acoustic impedance of the backing layer material is similar to that of the piezoelectric material, most of the backward transmitted wave quickly attenuates and become heat, and only a very small portion may bounce back. Commonly used backing layer materials include tungsten-loaded epoxy, pyrolytic, brass and carbon, etc. Although still playing the role of damping the backward waves, a proper matching layer can increase the energy transmitting efficiency from the front end so that less energy will be reflected. If the matching layer is optimized, the backing layer may not be needed. In fact, air backing designs may be used as is known in the art.

Encapsulation Layer or Other Covering

The device of the present invention may optionally include one or more encapsulation or barrier layers that isolate the light source and/or ultrasonic emitter (or other layers) from an ambient environment. The encapsulation or barrier layer is preferably substantially impermeable to moisture and oxygen. In general, the moisture and oxygen sensitive components should be enclosed by materials having gas permeation properties. The barrier preferably achieves low water vapor permeation rates of $10^{-4}$ g/m²/day or less, $10^{-5}$ g/m²/day or less, and even more preferably about $10^{-6}$ g/m²/day or less.

The encapsulation or barrier layer may be glass or a plastic, for example. Exemplary materials include a polyetheretherketone film commercially available from Victrex under the name APTIV. In still another aspect, the substrate is a thin film sold under the name Flexent by Konica Minolta or flexible glass such as Willow Glass by Dow Corning. Ideally substrates in direct contact with organic layers will have exceptional barrier capabilities that withstand heat, offer flexibility, have sustained reliability and can be mass produced.

The device may be further covered with a transparent or semi-transparent covering. The covering may provide comfort for a patient using the device particularly if the patient is lying on the device. The covering may provide protection to the device, keeping dirt and fluid off of the device and providing a cushion to protect the device from impact.

Arrays

In another aspect, the present invention is directed to a light and/or ultrasonic system comprising a plurality of the devices (each containing a light source and/or ultrasonic transducer as provided herein) arranged in an array and held in proximity to each other by a flexible, preferably transparent, material. The flexible material may be acoustically matched to the ultrasonic transducers of the devices in the array. The flexible material typically comprises a polymeric material selected from thermoplastics, thermosets, rubbers, or mixtures thereof. The flexible acoustically matched material will ordinarily be formed from a polymeric material, and optionally, a filler. The polymeric material should have good compatibility with the components of the transducer, biocompatibility, and flexibility. Suitable polymeric materials include thermoplastics such as high density polyethylenes, polymethyl methacrylates, polypropylenes, polybutylene terephthalates, polycarbonates, polyurethanes such as CA 118 and CA 128 available from Morton Chemical and estane polyester, and the like; thermosets such as epoxies, including Spurr epoxy and Stycast 80, Stycast 1365-65 and the like; and rubbers such as silicone rubbers such as dispersion 236 available from Dow Corning and RTV-141 available from Rhone-Poulenc, Inc. and the like. The flexible material may also comprise Kapton® polyimide film, which has stable mechanical, physical and thermal properties as well as high tensile strength and folding endurance suitable for use when wrapped around the human anatomy. If desired, the acoustic impedance of the polymeric materials may be increased by the incorporation of one or more fillers. Suitable fillers include PZT, tungsten, alumina, silica glass, tungsten carbide, titanium, glass powder and the like with glass powder being preferred. The size of the filler particles should be in the range of about 0.1 to about 50 microns and preferably from about 0.5 to about 5 microns. The amount of filler employed will be that amount necessary to impart the desired acoustic impedance. Normally, from about 2 to about 50 percent filler by volume and preferably from about 5 to about 30 percent filler by volume is employed. A preferred polymeric material is silicone rubber.

The devices within the array may be the same or different, for example in terms of the shape, size, light output and/or ultrasonic output. The devices within the array may produce ultrasound of different frequencies, power densities, duty factors and modulation frequencies. Such parameters of the devices may be pre-programmed into an electronic control module. Each of the devices within the array may be independently controlled by the control module. Each light source and/or ultrasonic transducer within each of the devices of the array may be independently controlled by the control module such that each device is capable of delivering light and ultrasound simultaneously or sequentially in pulsed or continuous modes.

The array can be programmed to deliver a desired sequence of light and/or ultrasound frequencies, in pulsed or continuous mode, in set patterns, thereby avoiding problems of over or under exposure of the skin to the light and/or ultrasound, which can cause overheating of the skin. The array is controllable such that light and/or ultrasound frequencies are capable of being driven so that the light and/or ultrasound field moves across the array in a preset, pseudorandom or random pattern and at a preset, pseudorandom, or random speed, for example 2-3 seconds from left to right across the full width (e.g., 5-10 cm) of the array then 2-3 seconds back again, i.e., 4-6 seconds cycle time; or into the centre of the array and then out again, especially if the array has a circular shaped geometry. The pattern can be varied within the same treatment session, e.g., left to right then up and down. The pattern may be random or pseudorandom to mimic a manual application of a single or multiple head transducer that is moved by a clinician over a treatment surface. The pattern may change based on sensor input dependent on the treatment being performed. For example, if an area becomes too hot, the pattern may be altered to decrease the time or exposure over that tissue area.

The use of an array such that the light and ultrasound field moves across the array in a preset pattern and at a preset speed offers several advantages. A major cause of potential damage to the skin is overheating in the superficial skin where a high density of collagenous tissue is located—this area rapidly absorbs ultrasound and may overheat if the light and ultrasound field is not continuously moved. Also, the preset speed of the light and ultrasound field should preferably correspond to the typical movement of a single light/transducer assembly over a typical treatment site of two times the dimensional surface area of the device. This enables a non-attended safe treatment without the need for constant movement of the device. Further, the movement of the light and ultrasound field will reduce and possibly prevent unstable cavitation from forming in the field that can lead to thermal damage in the tissue.

Compositions Containing Active Therapeutic and/or Cosmetic Agents

In one aspect, the device of the present invention may be used in conjunction with a therapeutic and/or cosmetic composition comprising a therapeutic and/or cosmetic agent to be applied to the skin, including lotions, gels, creams, ointments, foams, roll-on formulations, mousses, aerosol and non-aerosol sprays. The composition is pharmaceutically-acceptable such that the ingredients are suitable for use in contact with the barrier membrane (e.g., the skin or mucosa) without undue toxicity, incompatibility, instability, irritation, allergic response, and the like. The therapeutic and/or cosmetic composition is preferably transparent for transmission of the light generated by the light source of the device.

The therapeutic and/or cosmetic composition may be contained in a pad such as a gel pad or hydrogel pad. The composition may be applied prior to treatment with the device, or after treatment with the device. Preferably, the composition is present on the skin while the light and/or ultrasound generated by the device is being applied to the skin. As used herein, the term "cosmetic composition" is intended to describe compositions for topical application to human skin, including leave-on and wash-off products. The composition may be applied, for example, by pouring, dropping, or spraying, if a liquid; rubbing on, if an ointment, lotion, cream, gel, or the like; dusting, if a powder; spraying, if a liquid or aerosol composition; or by any other appropriate means. The term "skin" as used herein embraces the skin of the face, eyelids, eyebrows, forehead, lips, mouth, nose, ears, neck as well as the chest, arms, legs, hands, fingers, feet, toes, back, stomach, scalp, and the like.

The conditions that can be treated or otherwise addressed with the device of the present invention include various skin or cosmetic conditions including skin-aging, cellulite, enlarged pores, oily skin, folliculitis, precancerous solar keratosis, skin lesion, aging, wrinkled and sun-damaged skin, crow's feet, skin ulcers (diabetic, pressure, venous stasis), acne rosacea lesions, cellulite; photomodulation of sebaceous oil glands and the surrounding tissues; reducing wrinkles, acne scars and reducing acne bacteria, inflammation, pain, wounds, edema, Pagets disease, primary and metastatic tumors, connective tissue disease, manipulation of collagen, fibroblast, and fibroblast derived cell levels in mammalian tissue, illuminating retina, neoplastic, neovascular and hypertrophic diseases, inflammation and allergic reactions, perspiration, sweating and hyper-hydrosis from eccrine (sweat) or apocrine glands, jaundice, vitiligo, ocular neovascular diseases, bulimia nervosa, herpes, seasonal affective disorders, mood, sleep disorders, skin cancer, crigler naijar, atopic dermatitis, diabetic skin ulcers, pressure ulcers, relief of muscular pains, pain, stiffness of joints, reduction of bacteria, gingivitis, whitening teeth, treatment of teeth and tissue in mouth, wound healing. As used herein, the term "treating" or "treatment" means the treatment (e.g., whole or partial alleviation or elimination of symptoms and/or cure) and/or prevention or inhibition of the condition.

In one aspect, the cosmetic conditions that can be addressed with the device of the present invention are selected from acne, skin rejuvenation and skin wrinkles, cellulite, melisma (skin brown spots or discoloration), and vitiligo. Many therapeutic treatments also have a cosmetic component. Psoriasis, e.g., can be mild, mild-to-moderate, moderate, moderate-to-severe and severe. Any of these categories has a cosmetic component, which may be responsible for severe psychological problems of affected patients.

Examples of therapeutic and/or cosmetic agents that may be contained in the therapeutic and/or cosmetic composition of the present invention are described in Luebecke, U.S. Published Patent Application No. 2008/0051680 and Castel, U.S. Published Patent Application No. 2011/0040235, which are both incorporated herein by reference.

In another aspect, the therapeutic and/or cosmetic composition comprises an anti-glycation agent. Examples of anti-glycation agents include one or more of alanyl-L-histidine (L-carnosine), N-acetylcysteine, aminoguanidine, D-penicillamine, acetylsalicyclic acid (aspirin), paracetamol, indomethacin and ibuprofen and/or a functional derivative or prodrug thereof. Other examples include beta-alanylhistamine (carcinine), N-acetyl-beta-alanylhistamine (N-acetylcarcinine), L-prolyl histamine, N-acetyl-L-carnosine, and combinations thereof.

In one aspect, the cosmetic conditions that can be addressed with the device of the present invention include the treatment of acneiform eruptions. The term acneiform eruption refers to a group of dermatoses including acne vulgaris, rosacea, folliculitis, and perioral dermatitis. Acneiform eruptions are, generally spoken, caused by changes in the pilosebaceous unit and are selected from acne aestivalis (Mallorca acne), acne conglobata, acne cosmetics, acne fulminans (acute febrile ulcerative acne), acne keloidalis (acne keloidalis nuchae, dermatitis papillaris capillitii, folliculitis keloidalis, folliculitis keloidis nuchae, nuchal keloid acne), acne mecanica, acne medicamentosa, acne miliaris necrotica (acne varioliformis), acne vulgaris, acne with facial edema (solid facial edema), acneiform eruptions, blepharophyma, erythrotelangiectatic rosacea (erthemaotelangiectatic rosacea), excoriated acne (acne excoriée des jeunes filles, Picker's acne), glandular rosacea, gnathophyma, gram-negative rosacea, granulomatous facial dermatitis, granulomatous perioral dermatitis, halogen acne, hidradenitis suppurativa (acne inversa, Verneuil's disease), idiopathic facial aseptic granuloma, infantile acne, lupoid rosacea (granulomatous rosacea, micropapular tuberculid, rosacea-like tuberculid of Lewandowsky), lupus miliaris disseminatus faciei, metophyma, neonatal acne (acne infantum, acne neonatorum), occupational acne, ophthalmic rosacea (ocular rosacea, ophthalmorosacea), otophyma, persistent edema of rosacea (chronic upper facial erythematous edema, Morbihan's disease, Rosaceous lymphedema), pomade acne, papulopustular rosacea, perifolliculitis capitis abscedens et suffodiens (dissecting cellulitis of the scalp, dissecting folliculitis, perifolliculitis capitis abscedens et suffodiens of Hoffman), perioral dermatitis, periorbital dermatitis (periocular dermatitis), pyoderma faciale (rosacea fulminans), rhinophyma, rosacea (acne rosacea), rosacea conglobata, rosacea fulminans, SAPHO syndrome, steroid rosacea, tropical acne.

In one embodiment, the therapeutic and/or cosmetic composition comprises an anti-acne and/or anti-rosacea agent. Examples of anti-acne and anti-rosacea agents include, but are not limited to: retinoids such as tretinoin, isotretinoin, motretinide, adapalene, tazarotene, azelaic acid, and retinol; triclosan; chlorhexidine gluconate; salicylic acid; benzoyl peroxide; resorcinol; sulfur; sulfacetamide; urea; antibiotics such as tetracycline, clindamycin, metronidazole, erythromycin; anti-inflammatory agents such as corticosteroids (e.g., hydrocortisone), ibuprofen, naproxen, and hetprofen; imidazoles such as ketoconazole and elubiol; and salts and prodrugs thereof. Other examples of anti-acne active agents include: all forms of vitamin C (D-ascorbic acid, L-ascorbic acid or derivatives of ascorbic acid), all forms of tocopherol (vitamin E) or its derivatives, essential oils, alpha-bisabolol, dipotassium glycyrrhizinate, camphor, beta-glucan, allantoin, feverfew, flavonoids such as soy isoflavones, saw palmetto, chelating agents such as EDTA, lipase inhibitors such as silver and copper ions, hydrolyzed vegetable proteins, inorganic ions of chloride, iodide, fluoride, and their nonionic derivatives chlorine, iodine, fluorine, and other valences, synthetic phospholipids and natural phospholipids such as Arlasilk™ phospholipids CDM, SV, EFA, PLN, and GLA (Uniqema, ICI Group of Companies, Wilton, UK). Combinations of the foregoing are also within the scope of the present invention.

In another aspect, the therapeutic and/or cosmetic composition comprises an antioxidant. In general, antioxidants are substances which inhibit oxidation or suppress reactions promoted by oxygen or peroxides. Antioxidants, especially lipid-soluble antioxidants, can be absorbed into the cellular membrane to neutralize oxygen radicals and thereby protect the membrane. In one aspect, the anti-oxidant is selected from the group consisting of one or more of arginine, ascorbic acid, a prodrug or derivative of ascorbic acid, ascorbyl palmitate, magnesium ascorbyl phosphate, trisodium ascorbyl phosphate, anserine, carnosine, opidine, homocarnosine and/or acetylanserine. The antioxidants useful in the present invention are preferably selected from the group consisting of: all forms of tea or its extracts including, black, red, and green tea, all forms of vitamin A (retinol, palmitate), all forms of vitamin $A_2$ (3,4-didehydroretinol), all forms of carotene such as alpha-carotene, beta-carotene, gamma-carotene, delta-carotene, all forms of vitamin C (D-ascorbic acid, L-ascorbic acid, or derivatives of ascorbic acid), all forms of tocopherol such as vitamin E or its derivatives (alpha-tocopherol, 3,4-dihydro-2,5,7,8-tetramethyl-2-(4,8,12-trimethyltri-decyl)-2H-1-benzopyran-6-ol), beta-tocopherol, gamma-tocopherol, delta-tocopherol, tocoquinone, tocotrienol. In a preferred aspect, the therapeutic and/or cosmetic composition includes one or more of ascorbic acid (vitamin C) or alpha-tocopherol (vitamin E) or their pharmaceutically acceptable salts and esters.

In still another aspect, the therapeutic and/or cosmetic composition comprises hyaluronic acid (HA) or salt or derivative thereof. The composition may comprise high molecular weight HA (greater than $1\times10^6$ Da), low molecular weight HA (less than about $1\times10^6$ Da), or some combination thereof. The HA may have a molecular weight ranging between about 50 Da about to $2\times10^7$ Da (e.g., about 50, 100, 500, 1000, 5000, 10,000, 50,000, $1\times10^5$, $2\times10^5$, $3\times10^5$, $4\times10^5$, $5\times10^5$, $6\times10^5$, $7\times10^5$, $8\times10^5$, $9\times10^5$, $1\times10^6$ Da, $5\times10^6$ Da, $1\times10^7$ Da, $1.5\times10^7$ Da, $2\times10^7$ or some range therebetween). The therapeutic and/or cosmetic composition may comprise a low molecular weight HA (e.g., about 10, 50, 100, 200, 300, 400, 500, 600, 700, 800, 900, 1000, 10,000, 20,000, 30,000, 40,000, 50,000, 60,000, 70,000, 80,000, 90,000, $1\times10^5$, $2\times10^5$, $3\times10^5$, $4\times10^5$, $5\times10^5$, $6\times10^5$, $7\times10^5$ $8\times10^5$, $9\times10^5$, $1\times10^6$ Da or some range therebetween) in combination with a high molecular weight HA (e.g., about $1\times10^6$ Da, $5\times10^6$ Da, $1\times10^7$ Da, $1.5\times10^7$ Da, $2\times10^7$ Da or some range therebetween).

In one aspect, the device may be used in conjunction with a therapeutic and/or cosmetic composition comprising a hormone. Suitable hormones are, e.g., selected from estrogen, progestogen, a combination of estrogen and progestogen, cyproterone, oestrogen, a combination of cyproterone and estrogen, drospirenone, spironolactone, and cortisone. In another aspect, the therapeutic and/or cosmetic composition includes a retinoid, such as vitamin A derivatives such as isotretinoin, tretinoin, adapalene, tazarotene, isotretinoin, and retinol.

In one aspect, the device may be used in conjunction with a therapeutic and/or cosmetic composition comprising an anti-aging agent. Examples of suitable anti-aging agents include, but are not limited to: inorganic sunscreens such as titanium dioxide and zinc oxide; organic sunscreens such as octyl-methoxy cinnamates; retinoids; dimethylaminoathanol (DMAE), copper containing peptides, vitamins such as vitamin E, vitamin A, vitamin C, and vitamin B and vitamin salts or their derivatives such as ascorbic acid di-glucoside and vitamin E acetate or palmitate; alpha hydroxy acids and their precursors such as glycolic acid, citric acid, lactic acid, malic acid, mandelic acid, ascorbic acid, alpha-hydroxybutyric acid, alpha-hydroxyisobutyric acid, alpha-hydroxyisocaproic acid, atrrolactic acid, alpha-hydroxyisovaleric acid, ethyl pyruvate, galacturonic acid, glucoheptonic acid, glucoheptono 1,4-lactone, gluconic acid, gluconolactone, glucuronic acid, glucuronolactone, isopropyl pyruvate, methylpyruvate, mucic acid, pyruvic acid, saccharic acid, saccaric acid 1,4-lactone, tartaric acid, and tartronic acid; beta hydroxy acids such as beta-hydroxybutyric acid, beta-phenyl-lactic acid, and beta-phenylpyruvic acid; zinc and zinc containing compounds such as zinc oxides; and botanical extracts such as green tea, soy, milk thistle, algae, aloe, angelica, bitter orange, coffee, goldthread, grapefruit, hoellen, honeysuckle, Job's tears, lithospermum, mulberry, peony, puerarua, nice, and safflower; and salts and prodrugs thereof.

In one aspect, the device may be used in conjunction with a therapeutic and/or cosmetic composition comprising a depigmentation agent. Examples of suitable depigmentation agents include, but are not limited to: soy extract; soy isoflavones; retinoids such as retinol; kojic acid; kojic dipalmitate; hydroquinone; arbutin; transexamic acid; vitamins such as niacin and vitamin C or their derivatives; azelaic acid; linolenic acid and linoleic acid; placertia; licorice; and extracts such as chamomile and green tea; and salts and prodrugs thereof.

In one aspect, the device may be used in conjunction with a therapeutic and/or cosmetic composition comprising a plant extract. Examples of plant extracts include, but are not limited to: feverfew, soy, glycine soja, oatmeal, what, aloe vera, cranberry, hazel witch, alnus, arnica, artemisia capillaris, asiasarum root, birch, calendula, chamomile, cnidium, comfrey, fennel, galla rhois, hawthorn, houttuynia, hypericum, jujube, kiwi, licorice, magnolia, olive, peppermint, philodendron, salvia, sasa albo-marginata, natural isoflavonoids, soy isoflavones, and natural essential oils.

In one aspect, the device may be used in conjunction with a therapeutic and/or cosmetic composition comprising other active agents including those commonly used for topical treatment and in cosmetic treatment of skin tissues, such as topical antibiotics for wounds, topical antifungal drugs to treat fungal infections of the skin and nails, and antipsoriatic drugs to treat psoriatic lesions of the skin and psoriatic nails.

Examples of antifungal drugs include, but are not limited to: miconazole, econazole, ketoconazole, sertaconazole, itraconazole, fluconazole, voriconazole, clioquinol, bifoconazole, terconazole, butoconazole, tioconazole, oxiconazole, sulconazole, saperconazole, clotrimazole, undecylenic acid, haloprogin, butenafine, tolnaftate, nystatin, ciclopirox olamine, terbinafine, amorolfine, naftifine, elubiol, griseofulvin, and their pharmaceutically acceptable salts and prodrugs.

Examples of antibiotics (or antiseptics) include, but are not limited to: mupirocin, neomycin sulfate bacitracin, polymyxin B, 1-ofloxacin, tetracyclines (chlortetracycline hydrochloride, oxytetracycline-10 hydrochloride and tetrachcycline hydrochoride), clindamycin phosphate, gentamicin sulfate, metronidazole, hexylresorcinol, methylbenzethonium chloride, phenol, quaternary ammonium compounds, tea tree oil, and their pharmaceutically acceptable salts and prodrugs.

Examples of antimicrobials include, but are not limited to: salts of chlorhexidine, such as lodopropynyl butylcarbamate, diazolidinyl urea, chlorhexidine digluconate, chlorhexidine acetate, chlorhexidine isethionate, and chlorhexidine hydrochloride. Other cationic antimicrobials may also be used, such as benzalkonium chloride, benzethonium chloride, triclocarban, polyhexamethylene biguanide, cetylpyridium chloride, methyl and benzethonium chloride. Other antimicrobials include, but are not limited to: halogenated phenolic compounds, such as 2,4,4'-trichloro-2-hydroxy diphenyl ether (Triclosan); parachlorometa xylenol (PCMX); and short chain alcohols, such as ethanol, propanol, and the like.

Examples of antipsoriatic drugs or drugs for seborrheic dermatitis treatment include, but are not limited to: corticosteroids (e.g., betamethasone dipropionate, betamethasone valerate, clobetasol propionate, diflorasone diacetate, halobetasol propionate, triamcinonide, dexamethasone, fluocinonide, fluocinolone acetonide, halcinonide, triamcinolone acetate, hydrocortisone, hydrocortisone valerate, hydrocortisone butyrate, alclometasone dipropionate, flurandrenolide, mometasone furoate, methylprednisolone acetate), methotrexate, cyclosporine, calcipotriene, anthraline, shale oil and derivatives thereof, elubiol, ketoconazole, coal tar, salicylic acid, zinc pyrithione, selenium sulfide, hydrocortisone, sulfur, menthol, and pramoxine hydrochloride, and salts and prodrugs thereof.

Examples of anti-inflammatory agents include, but are not limited to: suitable steroidal anti-inflammatory agents such as corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and salts are prodrugs thereof. The preferred steroidal anti-inflammatory for use in the present invention is hydrocortisone. A second class of anti-inflammatory agents which is useful in the compositions of the present invention includes the nonsteroidal anti-inflammatory agents.

Other active agents include, but are not limited to: wound healing enhancing agents, such as recombinant human platelet-derived growth factor (PDGF) and other growth factors, ketanserin, iloprost, prostaglandin $E_1$ and hyaluronic acid, scar reducing agents such as mannose-6-phosphate, analgesic agents, anesthetics, hair growth enhancing agents such as minoxidil, hair growth retarding agents such as eflornithine hydrochloride, antihypertensives, drugs to treat coronary artery diseases, anticancer agents, endocrine and metabolic medication, neurologic medications, medication for cessation of chemical additions, motion sickness, protein and peptide drugs.

The amount of the active agent in the therapeutic and/or cosmetic composition will depend on the active agent and/or the intended use of the device. In one embodiment, the carrier contains a safe and effective amount of the active agent, for example, from about 0.001 percent to about 20 percent, by weight, such as from about 0.01 percent to about 5 percent, by weight, of the carrier. As used herein, "safe and effective amount" means an amount of the ingredient or of the composition sufficient to provide the desired benefit at a desired level, but low enough to avoid serious side effects. The safe and effective amount of the ingredient or composition will vary with the area being treated, the age and skin type of the end user, the duration and nature of the treatment, the specific ingredient or composition employed, the particular pharmaceutically-acceptable carrier utilized, and like factors.

In one aspect, for the treatment of acne, the device of the present invention preferably emits light in the range between about 350 and 900 nm, preferably between about 380 and 850 nm, more preferably between about 400 and 850 nm, and even more preferably between about 400 and 830 nm. Further, the preferred light for the treatment of acne is purple light. The preferred purple light has emission wavelengths for the treatment of acne of about 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429 and 430 nm. For example, 414 and 415 nm are particularly suitable in order to kill *P. acnes* bacteria and to help cure existing blemishes and to prevent further outbreaks. Studies on the application of phototherapy to treat acne have revealed that a combination of different wavelengths or ranges of wavelengths are particularly suitable to treat acne efficiently. For example, a combination of red light and purple light is may be used to treat acne. The red light is preferably selected from the range between about 590 to 750 nm, more preferably between about 600 and 720 nm, and even more preferably between 620 and 700 nm. Two further preferred wavelengths for the treatment of acne are 633 and 660 nm. The light at about 633 to 660 nm increases cellular metabolism, triggers collagen synthesis for scar repair and remodeling and increases Superoxide dismutase which acts as an oxygen radical scavenger, which decreases inflammation. A further effect is the increase of nitric oxide (NO) synthesis which increases microvascular perfusion further impacting the cleansing and washout of tissues where inflammatory substances have aggregated. The purple light can be selected from the wavelengths as described above.

The ultrasonic energy should be applied over the treatment site (such as an acne-infected skin) preferably in the range of about 2 kHz to 200 kHz and more preferably in the 45 to 90 kHz range. These frequencies provide the breakup of bacterial plaque to further cleanse the tissue, while opening channels through the stratum corneum allowing the passage of therapeutic active agents. Thus, the effects of the light, ultrasound and active therapeutic/cosmetic agent act in a synergistic fashion and are complimentary. Additionally, heat may be provided using a heater layer in contact with the skin to treat acne eruptions in an effective manner. Electrical current may also be applied to add an iontophoretic component to assist the drive of the therapeutic active agents assuming they are ionic.

For the treatment of whiteheads, the device preferably emits light of about 500 nm or light in the range between 500 and 700 nm. A whitehead, which is also called closed comedone, is a follicle that is filled with the same material, sebum, but has a microscopic opening to the skin surface. Since the air cannot reach the follicle, the material is not oxidized, and remains white. This is an application where the heating element of the present invention is particularly effective.

In another aspect, for the treatment or prevention of cellulite, the device preferably emits light in the range between 400 and 1000 nm, preferably in the range between 400 and 900 nm, more preferably in the range between 450 and 900 nm, and even more preferably in the range between 500 and 850 nm. For the treatment or prevention of cellulite, the device preferably applies ultrasound at a frequency of between about 25 kHz and 80 kHz to cause a breakup of the cellulite matrix. Cellulite describes a condition that is claimed to occur in most women, where the skin of the lower limbs, abdomen, and pelvic region becomes dimpled. The use of high frequency ultrasound at about 1 to 5 MHz is also effective in heating the areas of cellulite to liquefy the structure which can then through retrograde massage be reabsorbed in the lymphatic channels. The low frequency ultrasound opens channels through the stratum corneum allowing the passage of therapeutic active agents that assist in the breakup and reabsorption of the cellulite matrix. Thus, the effects of the light, ultrasound and active therapeutic and/or cosmetic agent act in a synergistic fashion and are complimentary. Additionally, heat may be provided using a heater layer in contact with the skin which assists in the liquefaction of the cellulite matrix.

For the treatment or prevention of skin aging and fine lines and wrinkles, the device preferably emits light in the range between 400 and 950 nm. Preferably, the wavelength is in the range between 550 and 900 nm, such as between 600, 630, 660 or some range therebetween. In another aspect, for the treatment and/or prevention of skin aging, the device emits infrared light in the range between 780 and 1060 nm. The light at about 633 to 660 nm increases cellular metabolism, triggers collagen synthesis for scar repair and remodeling and increases Superoxide dismutase which acts as an oxygen radical scavenger, which decreases inflammation. A further effect is the increase of NO synthesis which increases microvascular perfusion further impacting the cleansing and washout of tissues where inflammatory substances have aggregated while improving tissue nutrition. The use of pulsed subthermal high frequency ultrasound at about 1 to 5 MHz at 20% duty factors in the range of 0.5 w/cm$^2$ is also effective in stimulating tissue regeneration and is often used in this application. The low frequency ultrasound opens channels through the stratum corneum allowing the passage of therapeutic active agents such as vitamin C, hyaluronic acid large, and other actives agents that assist in the rebuilding of the collagen and elastin matrix. Thus, the effects of the light, ultrasound and active therapeutic and/or cosmetic agent act in a synergistic fashion and are complimentary. Additionally, heat may be provided using a heater layer in contact with the skin which assists further in the treatment of wrinkles through a heat and stretch mechanism. That is, once the tissue reaches the viscoelastic temperature of about 40-41° C., manual stretching of the wrinkle tends to iron it out. If the stress is maintained during cool down, the wrinkle will flatten and maintain the new elongation of the collagen. In another aspect, electrical current can be applied to provide additional iontophoretic drive in combination with the low frequency ultrasound to further penetrate the active agents. If the current is an AC or pulsed current, it may be used to decrease muscle disuse atrophy or muscle hypertonicity to remodel the underlying muscle structure and thereby decrease wrinkles in a similar manner (with respect to the aesthetic result) that Botox or muscle exercise would affect the tissue structure.

In one aspect, the composition includes a photosensitizing medicine for use in phototherapy treatments. In this case, the device activates the photosensitizing medication. The photosensitizing medicine can be a liquid, cream or intravenous drug. For pre-cancer or cancer treatment, for example, the photosensitizing medicine is preferably absorbed by atypical or cancerous cells. When the photosensitizing medicine is irradiated with light, activated oxygen molecules are produced which can destroy nearby cells. The ultrasonic field provides transport of the therapeutic medication through the stratum corneum to increase its efficacy as opposed to topical application.

In another aspect, the composition is a polymerizable composition that is polymerized under the action of the light generated from the light source, such as in Samain, European Patent No. 2252256. Thus, in an exemplary embodiment, the invention is directed to a cosmetic treatment method comprising: (a) depositing a composition on the skin, said composition being polymerizable under the action of a light stimulus; (b) placing the device of the present invention (such as in the form of a patch, bandage, and the like) over the composition; and (c) directing a light from the device to cause polymerization of the composition.

Modulation of Frequencies for Transdermal Transport

As discussed above, the low frequency ultrasound provided by the device provides cavitational effects in the skin, which improves drug delivery into and through the skin. It will be appreciated that the ultrasound source comprises an ultrasonic transducer that may be operated at different frequencies in order to maximize or otherwise improve transport of various therapeutic and/or cosmetic agents in a composition. For example, it will be appreciated that therapeutic and/or cosmetic agent "A" may be optimally transported at ultrasound frequency $f_A$ with an optional ultrasound modulation frequency $f_{MA}$ while therapeutic and/or cosmetic agent "B" may be optimally transported at ultrasound frequency $f_B$ with an optional ultrasound modulation frequency $f_{MB}$. The different ultrasound frequencies (and optional ultrasound modulation frequencies) result in different cavitation effects and create different sizes of distortions in the stratum corneum, allowing different sizes of molecules and compounds to pass through the skin. Thus, the present invention contemplates that the ultrasound frequencies and/or the modulation frequencies can be varied continuously or in stages during operation. That is, the present invention contemplates that the transducer can operate at multiple frequencies (e.g., continuously over a selected range of frequencies or at one or more pre-determined frequencies).

Further, the device may be programmed using an electronic control module to operate in cycles of different frequencies that correspond to those associated with the various therapeutic and/or cosmetic agents. For example, the device may be programmed to operate at an ultrasound frequency $f_A$ for a first period of time (in order to maximize transport of therapeutic and/or cosmetic agent A) and then operate at an ultrasound frequency $f_B$ for a second period of time (in order to maximize transport of therapeutic and/or cosmetic agent B). As another example, the device may be programmed to operate at an ultrasound frequency $f_A$ with an ultrasound modulation frequency of $f_{MA}$ for a first period of time (in order to maximize transport of therapeutic and/or cosmetic agent A) and then operate at an ultrasound frequency $f_{B-US}$ with an ultrasound modulation frequency $f_{MB}$ for a second period of time (in order to maximize transport of therapeutic and/or cosmetic agent B). As yet another example, the device may be operated at an ultrasound frequency $f_A$ with an ultrasound modulation frequency of $f_{MA}$ for a first period of time followed by a change in the ultrasound modulation frequency only to $f_{MB}$ for a second period of time. The cycling and patterns of the frequency provides significant benefits in transporting compositions containing multiple therapeutic and/or cosmetic agents through the skin surface. The amount of time at each frequency may also be programmed into the electronic control module based on the percentage composition of the therapeutic and/or cosmetic agent and the diffusion rate through the skin for the therapeutic and/or cosmetic agent. It will be appreciated that multiple therapeutic and/or cosmetic agents may be delivered using similar techniques to optimize each therapeutic and/or cosmetic agent.

In another aspect, the light source may be pulsed at various frequencies, including the modulation or fundamental frequency of the ultrasonic transducer. The pulsation is preferably synchronized to maximize cavitation effects on the cellular membranes and the stratum corneum. The wavelength of the light is selected to optimize the healing and biostimulative effects in the tissue and the light modulation frequencies are synchronized with the frequencies of the ultrasonic modulation or the fundamental frequency of the ultrasonic transducer. This synergistic effect enhances the shear waves and cavitation effects in the tissue when the light source is pulsed synchronously with the ultrasonic wave modulation.

Thus, it will be appreciated that the light source of the device may be operated at different wavelengths modulated at different frequencies in order to maximize transport of various therapeutic and/or cosmetic agents in a composition.

For example, it will be appreciated that therapeutic and/or cosmetic agent "A" may be optimally transported at light wavelength $\lambda_A$ and pulsed with an optional light modulation frequency $f_{MA}$ while therapeutic and/or cosmetic agent "B" may be optimally transported at wavelength 4 with an optional light modulation frequency $f_{MB}$. The different light wavelengths (and optional light modulation frequencies) result in different cavitation effects and create different sizes of distortions in the stratum corneum, allowing different sizes of molecules and compounds to pass through the skin. Thus, the present invention contemplates light having various wavelengths and the modulation frequencies can be varied continuously or in stages during operation. That is, the present invention contemplates that the light source can operate at multiple wavelengths (e.g., over a selected range of wavelengths or at one or more pre-determined wavelengths). Further, the device may be programmed using the electronic control module to operate in cycles of different wavelengths that correspond to those associated with the various therapeutic and/or cosmetic agents. For example, the device may be programmed to operate at a light wavelength $\lambda_A$ for a first period of time (in order to maximize transport of therapeutic and/or cosmetic agent A) and then operate at a light wavelength $\lambda_B$ for a second period of time (in order to maximize transport of therapeutic and/or cosmetic agent B). As another example, the device may be programmed to operate at a light wavelength $\lambda_A$ with a light modulation frequency of $f_{MA}$ for a first period of time (in order to maximize transport of therapeutic and/or cosmetic agent A) and then operate at a light wavelength $\lambda_B$ with a light modulation frequency $f_{MB}$ for a second period of time (in order to maximize transport of therapeutic and/or cosmetic agent B). As yet another example, the device may be operated at a light wavelength $\lambda_A$ with a light modulation frequency of $f_{MA}$ for a first period of time followed by a change in the light modulation frequency only to $f_{MB}$ for a second period of time. This may be repeated for third, fourth, fifth times, etc. for other active agents. The cycling and patterns of the light energy wavelengths and modulation frequencies provide significant benefits in transporting compositions containing multiple therapeutic and/or cosmetic agents through the skin surface. The amount of time at each wavelength and/or modulation frequency may also be programmed into the electronic control module based on the percentage composition of the therapeutic and/or cosmetic agent and the diffusion rate through the skin for the therapeutic and/or cosmetic agent.

To ascertain the appropriate modulation of the ultrasound for a given therapeutic and/or cosmetic agent, microdialysis can be used. Likewise, the effects of pulsing the light at various modulation frequencies may also be determined using this method. In general, a composition containing the therapeutic and/or cosmetic agent is placed on the skin or tissue surface in a conductive ultrasound gel. The ultrasonic transducer is placed over the composition and the skin or tissue, and the transducer is activated at the appropriate dose and test frequency. Sterile water is pumped through a microdialysis probe implanted approximately 2 mm under the skin under the transducer. See, e.g., Klimowicz, *Evaluation of Skin Penetration of Topically Applied Drugs in Humans by Cutaneous Microdialysis*, J Clin Pharm Ther. April; 32 (2):143-8 (2007); and Ault et al., *Microdalysis Sampling for the Investigation of Dermal Drug Transport*, Pharm Res. October 9 (10):1256-61 (1992).

The ultrasound frequencies, ultrasound modulation frequencies, light wavelengths, and light modulation frequencies that have been optimized for the transdermal delivery for each therapeutic and/or cosmetic agent of interest are programmed into the electronic control module. Thus, it is contemplated that the device can apply a frequency (ultrasound and light) for each therapeutic and/or cosmetic agent. That is, assuming that the transdermal delivery of therapeutic and/or cosmetic agent A is optimal at a first ultrasonic frequency $f_A$ (with an optional ultrasonic modulation frequency $f_{MA}$) and a first light wavelength $\lambda_A$ (with pulsing at an optional light modulation frequency of $f_{MA}$) and the transdermal delivery of therapeutic and/or cosmetic agent B is optimal at a second ultrasonic frequency $f_B$ (with an optional ultrasonic modulation frequency $f_{MB}$) and a second light wavelength $\lambda_B$ (with pulsing at an optional light modulation frequency of $f_{MB}$), then the device is programmed to operate in at least both modalities. In one aspect, the ultrasound and light are modulated at the same frequency.

Phototherapy

The device of the present invention can be used to provide phototherapy to a patient. As a result of the wavelength of the light, and the frequency of pulsation, and the energy delivery from the light source, there results in the body a large number of physiological responses. These physiological responses include, for example, acceleration of the production of procollagen resulting in enhanced collagen synthesis through selective action on collagen gene expression at the transcriptional level. This is a likely sequel to elevations of procollagen mRNA levels resulting in alterations in the chromatin structure. There is also theorized to be increased cross-linking of existing collagen molecules and improved organization of functional collagen fibers. Also, it is theorized that the device stimulates macrophages (a type of white blood cell) to release factors that stimulate fibroblast replication and proliferation (e.g., monokines). Cellular effects which occur include mitochondrial hyperplasia, the appearance of cytoplasmic microfilament bundles, and the deposition of an abundant fibrillar matrix in pericellular regions. A cellular phenotype of the fibroblast, the myofibroblast, is generated. This cell is found in granulation tissue, and its primary role occurs in the remodeling phase of wound healing, including contractile activity in addition to the synthesis of collagen. The photothermal treatment device thereby accelerates the formation of a functional scar. See generally, Shapiro, U.S. Pat. No. 6,187,029. Pulsed light or ultrasonic stimulation also has the ability to stimulate underlying neural tissue, including sympathetic, parasympathetic and sensory nerves. Depending on the pulse parameters selected, nerves may be selectively stimulated to increase or decrease circulation and blood flow to assist in the treatment of tissue repair or modulation of inflammatory response or blocking or reabsorprion of edema. The device of the present invention may be programmed with a variety of wavelengths, ultrasound frequencies, duty factors, pulse rates and amplitudes to achieve the desired physiological effects described herein.

In another aspect, the device is well adapted to provide light energy, ultrasound, and heating of about 1 to 4° C. (e.g., via light energy from the light source, ultrasound from the high frequency ultrasonic transducer, and heat from the flexible transparent heater layer, or combinations thereof). It is known that high frequency ultrasound causes thermal effects in the skin and superficial tissue. This heat applied to the tissue triggers HSPs which act to reduce cellular death due to ultraviolet light exposure. Among other things, light energy in the near infrared and red visible regions provides a photoprotective effect on the subsequent lethal effects of exposure to UV light. The combination is highly synergistic to reducing UV photoaging and repairing its effects. If the device is also used with low frequency ultrasound, phonophoresis of Vitamin C and other substances can be effected to further accelerate the repair and photoprotective process.

Power Supply, Drive Circuit and Control Module

Each device of the present invention is driven and controlled by an electronic circuit that includes a power supply, drive circuit and control module. The electronic circuit may be provided in a separate housing electrically connected to the device or may be built into the flexible material that mounts the device or an array of the devices.

The power supply may be any power supply capable of supplying sufficient power to activate the light source, the ultrasonic transducer(s), the heater layer and/or the electrical stimulation layer of each device. The power supply may comprise a disposable or rechargeable battery, solar cell, fuel cell, an adapter, or may be powered by the power grid. The light source is preferably driven by DC or pulsed DC; however, the light source may alternatively be driven by AC. The ultrasonic transducer(s) are preferably driven by AC to deliver the low and/or high frequency ultrasound, although pulsed DC may be used to deliver low frequency ultrasound. The heater layer may be driven by AC, DC or pulsed DC to cause resistive heating across the device. The electrical stimulation layer is preferably driven by DC or pulsed DC to provide iontophoresis, or may be driven by pulsed AC or pulsed DC to provide relaxation or toning of the muscles. It should be understood that the electrical stimulation layer typically functions as a conductive electrode and is used in combination with a conductive return electrode to provide the desired electrical stimulation, as discussed above. One skilled in the art will understand that the output voltages and current levels of the DC, AC, pulsed DC and pulsed AC referenced above control the peak output of each layer of the device, which in combination with the treatment time control the dose.

Figure 12:
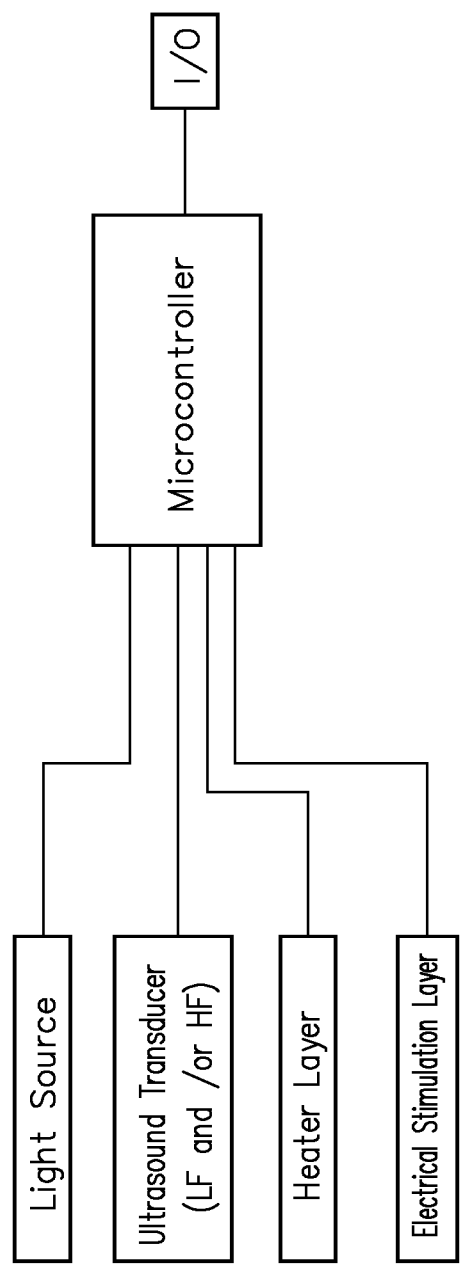
FIG. 12 is a block diagram of a first exemplary electronic circuit for controlling the device of the present invention, which includes an internal control module that is preprogrammed to provide a fixed dose.

In one embodiment, the control module is incorporated into the electronic circuit connected to the device or built into the flexible material that mounts the device (referred to as an "internal control module"). FIG. 12 is a block diagram of an exemplary electronic circuit for this embodiment. As can be seen, the device includes a light source, an ultrasonic transducer (low frequency and/or high frequency), a heater layer, and a conductive/electrical stimulation layer. Of course, it should be understood that the device could include only one or any combination of these elements. In one aspect, the device includes only a light source. In another aspect, the device includes only a low frequency ultrasonic transducer. In another aspect, the device includes only a high frequency ultrasonic transducer. In yet another aspect, the device includes only a dual frequency ultrasonic transducer. Other combinations will be apparent to one skilled in the art.

Each element of the device is independently controlled by a microcontroller (discussed below). Some elements may be directly connected to the microcontroller (DC output from the microcontroller), some elements may be connected to the microcontroller through an amplifier (AC output from the microcontroller), and some elements may be connected to the microcontroller through an oscillator that converts DC to AC in combination with an amplifier (DC output from the microcontroller). It should be understood that a variety of other circuit designs are possible and within the knowledge of one skilled in the art. The microcontroller is connected to one or more I/O devices, such as an LED that provides an indication of whether the device is on/off or an audio buzzer that alerts the user upon completion of a particular treatment. An on/off switch may also be provided to power the device.

Each element of the device is independently controlled by a microcontroller in accordance with a preprogrammed treatment cycle that provides a sequence of light, ultrasound, heat and/or electrical stimulation at a fixed dose. For example, the microcontroller may be preprogrammed for treatment of a specific cosmetic disorder, such as acne, psoriasis, and the like. The microcontroller may independently control the light source by adjusting the activation and deactivation of the light source, voltage, current, light wavelength, pulse width, modulation frequency, duty factor, and light treatment time. Likewise, the microcontroller may independently control an ultrasonic transducer by adjusting the activation and deactivation of the transducer, ultrasound treatment time, ultrasound frequency, ultrasound modulation frequency, etc. In addition, the microcontroller may control the electrical stimulation output for iontophoresis, as well as the temperature of the heater layer by adjusting the drive current to the graphene embedded in the layer. One skilled in the art will appreciate that other operating parameters may also be controlled by the microcontroller in accordance with the present invention.

Figure 13:
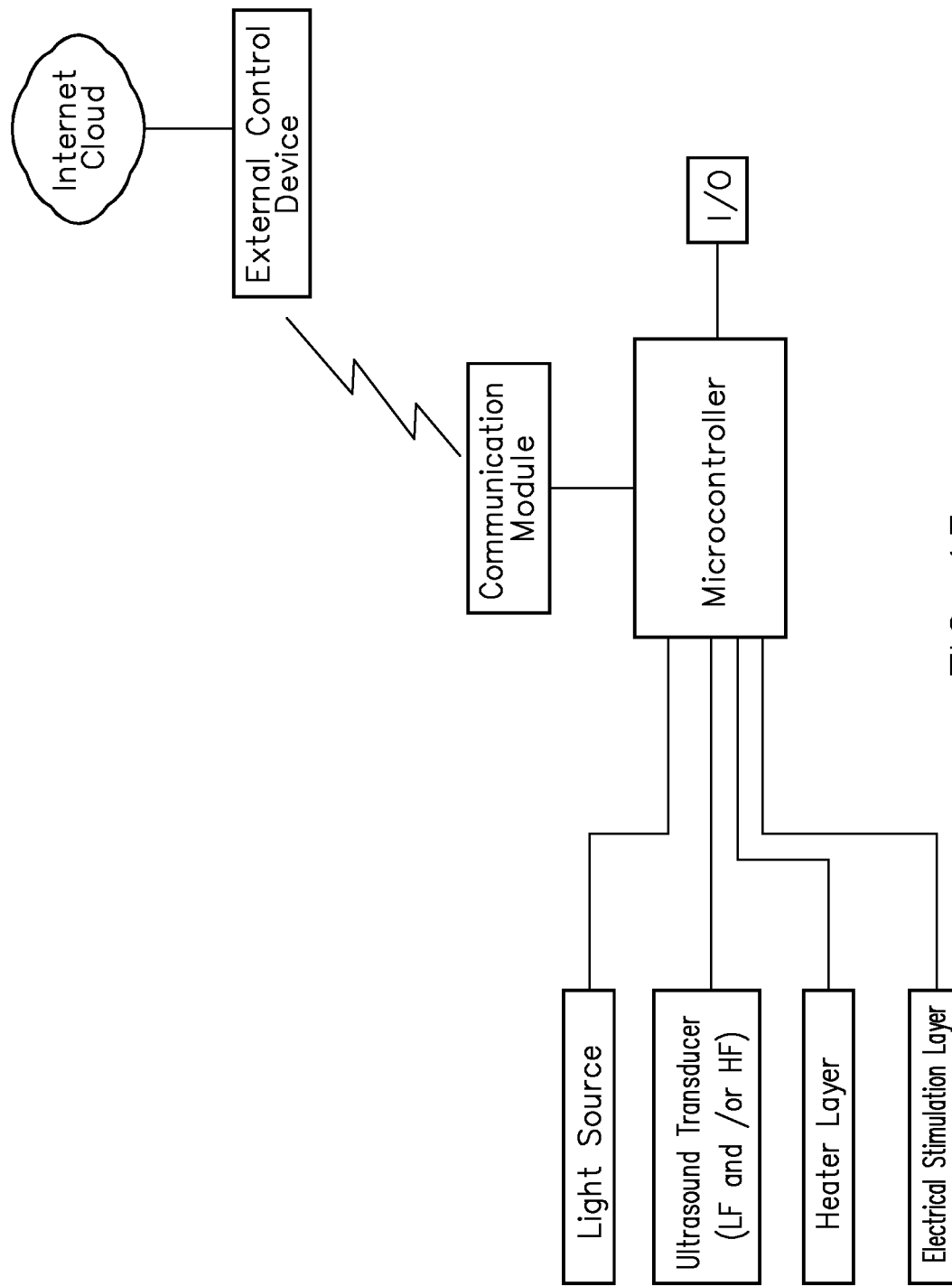
FIG. 13 is a block diagram of a second exemplary electronic circuit for controlling the device of the present invention, which includes an external control module that enables manual adjustment of the device parameters.

In another embodiment, all or a portion of the control functionality is provided by an external control device (referred to as an "external control module") that enables manual adjustment of the operating parameters of the device based on user input. FIG. 13 is a block diagram of an exemplary electronic circuit for this embodiment. As can be seen, the electronic circuit is similar to that shown and described in connection with FIG. 12, with the exception that the control functionality is not preprogrammed into the microcontroller. Instead, the microcontroller is connected to a communication module that enables wired or wireless communication with an external control device. The external control device may comprise a mobile communication device (e.g., a smart phone), a tablet computer, a laptop computer or any other device capable of executing a suitable control application. The external control device may in turn communicate over a communication network (e.g., the Internet cloud) in order to access applications or data hosted on a remote server. The communication module may communicate with the external control device over any suitable communication system, including network, USB and serial port communications, custom connectors and protocols such the iPhone or iPad connectors, Radio Frequency Identification (RFID), TransferJet, Dedicated Short Range Communications (DSRC), EnOcean, Near Field Communication (NFC), wireless sensor networks, ZigBee, EnOcean, Personal Area Networks (PAN), Wireless Personal Area Networks (WPAN) such as IrDA, Wireless USB, Bluetooth, Z-Wave, ZigBee, or Body Area Network, Wireless Sensor Networks (WSN), Ultra-Wideband (UWB) (such as UWB from WiMedia Alliance), Wireless Local Area Networks (WLAN) such as Wi-Fi products based on IEEE 802.11 standards, High Performance Radio LAN (HiperLAN), Wireless Metropolitan Area Networks (WMAN), Local Multipoint Distribution Service (LMDS), Worldwide Interoperability for Microwave Access (WiMAX), and High Performance Radio Metropolitan Area Network (HiperMAN). In a preferred aspect, the communication module communicates with the external control device via a low energy Bluetooth connection. As can be seen, the microcontroller is also connected to one or more I/O devices (as described above), including a touchscreen display that enables direct control of the device or operates as a slave to the external control device. As such, the control module may comprise a combination of an external control module (via the external control device) and an internal control module (via the touchscreen display). The external control device may also be connected to the Internet cloud where it can access stored data from previous use by the user or other users of the device, more intensive computing to evaluate treatment parameters and for user data management. The external control device may also be used to take photographs of the user's skin or other body parts and use sensors present in the external control device to provide further data sources for the user data which can be maintained in the device or in the cloud.

In this embodiment, the control module is controlled via an input device to enable manual adjustment of the operating parameters of each of the elements of the device. The input device may be provided on the external control device (via a keyboard, keypad, mouse, touchscreen display, buttons, or other input devices) or on one of the I/O devices (e.g., the touchscreen display) of the electronic circuit. The input device may enable selection of the treatment to be provided, the treatment time, the intensity of the treatment, treatment dose, the spectral output of the device, the age of the patient and/or the cosmetic application. The input device may show the system diagnostics, verification of the interface type (i.e., validation that the therapeutic and/or cosmetic composition, such as one present in a gel or gel pads, is matched to the device and authenticated as meeting the required specifications and authenticity, and are in appropriate contact to the skin). The input device may demonstrate sensor information relative to pre-therapeutic and post-therapeutic efficacy and safety information during operation. The input device may also enable entry of desired control points or manual adjustment of the settings, such as target, maximum and/or minimum temperature, light intensity, ultrasound intensity, and time of treatment. The system software may maintain archived patient/client data including treatment records, sensor data, treatment recommendations (e.g., the patient should drink more water if the patient is dehydrated, the patient should apply a certain therapeutic and/or cosmetic composition to the patient's skin based on skin melanin content), photography and other user data which may be obtained from the input devices.

The control module also includes a screen or other type of output device that may be used to communicate dosing information, display information on device performance, and set certain operating parameters of the device. The screen may also provide information concerning the treatment, the temperature of one or more locations on the patient, the exposure area of patient, the length of the treatment cycle, the time remaining in the treatment cycle, the light intensity setting of the light source, the ultrasound intensity setting of the transducer, the cumulative time of multiple treatments by the device, and other information concerning the settings and operation of the device. The screen may also provide information concerning preprogrammed treatment cycles for various phototherapy treatments.

The device may be used in a number of treatment sessions that together result in an overall treatment time. For such cases, the control module may include at least one timer configured to measure session time and overall treatment time or both. The timer may be used simply to monitor the session time or overall treatment time or may be used to deactivate the device after completion of a session or overall treatment.

Figure 14:
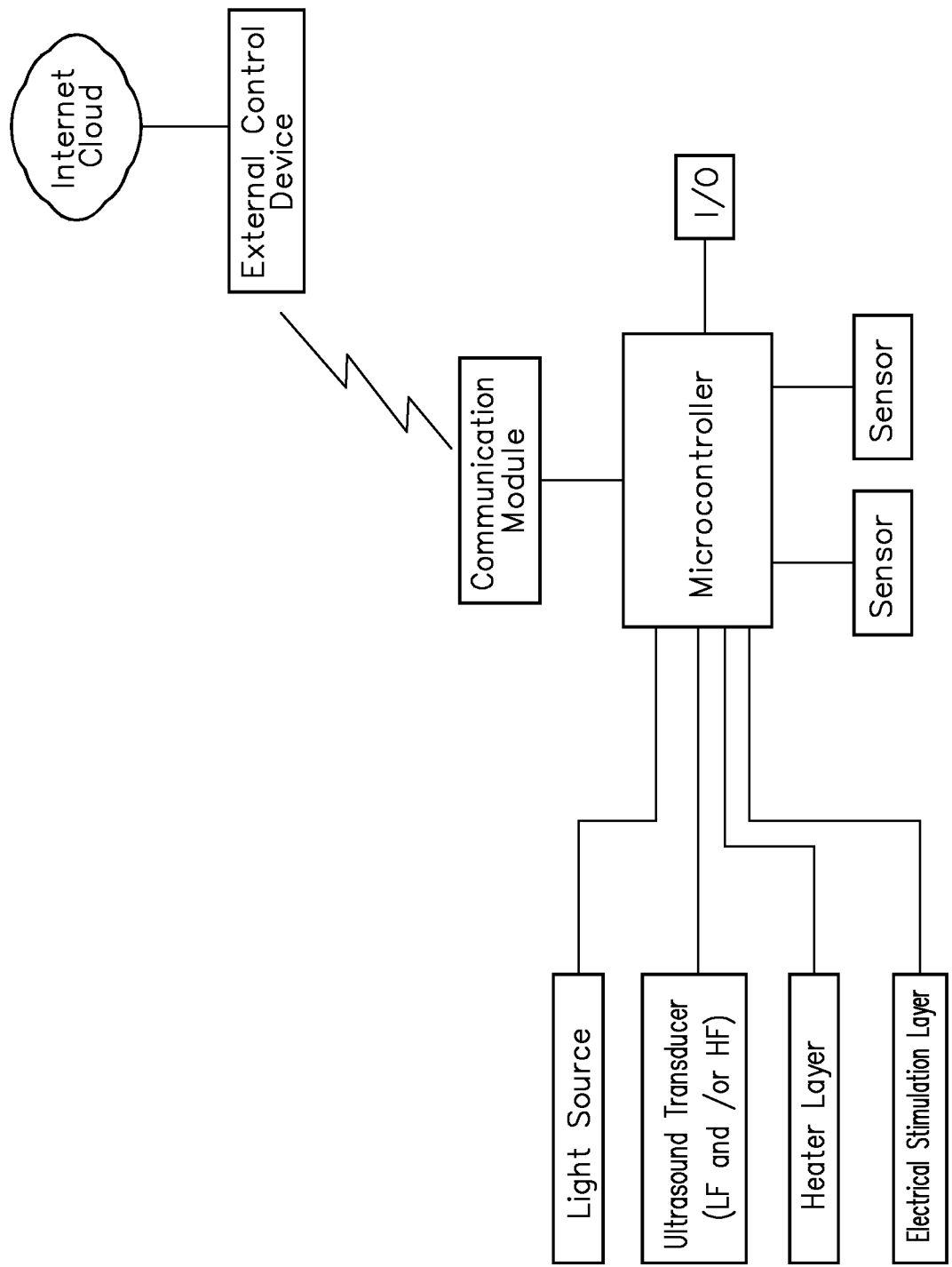
FIG. 14 is a block diagram of a third exemplary electronic circuit for controlling the device of the present invention, which includes sensors that provide feedback to enable automatic adjustment of the device parameters.

In another embodiment, the control module may operate based upon preprogrammed treatment cycles or allow dynamic control of a treatment cycle based upon user input or input from various sensors connected to the control module. FIG. 14 is a block diagram of an exemplary electronic circuit for this embodiment. As can be seen, the electronic circuit is similar to that shown and described in connection with FIG. 13, with the addition of one or more sensors that operate in a closed loop to provide feedback to the microcontroller. The feedback may comprise various types of signals, for example, electrical, chemical, mechanical, or pneumatic, that correspond to the parameter being sensed. Exemplary sensors include, but are not limited to, impedance measurement sensors, RFID sensors, digital signature sensors, temperature sensors, light emission spectrum sensors, pressure sensors, light intensity sensors, infrared temperature sensors, electrical impedance sensors, ultrasonic transmitters and receivers, skin hydration sensors, skin sebum level sensors, skin melanin content sensors, skin elasticity sensors, skin pH sensors, skin color sensors, skin glossiness sensors, skin friction sensors, and skin fluorescence sensors, as well as other sensors known in the art. Certain sensors may be built into the layers of the device, while other sensors may be applied to the tissue surface and protrude through the hydrogel.

The sensors may be used alone or in combination, for example, to determine the patient's overall exposure to a treatment by sensing the intensity of the light wavelengths and ultrasound frequencies over time and the total exposure of all light and ultrasound over time. The sensors may be used in a positive or negative feedback loop to control dosage and monitor effectiveness of the device for a desired application.

As an example, measurement of skin fluorescence would allow monitoring of the survival of the acne bacterium, whereby the dose would be varied or terminated based on the bacterial kill rate. The acne bacterium gives off a florecense in the red spectrum of 600-700 nm (typically 630 nm) when illuminated with purple light of around 400-450 nm (typically 415 nm). If a photo sensor is used to detect the red wavelength, then the feedback can be used to control the dose, i.e., a longer dose until the desired kill percentages occur. Detection diodes using diode printed inks could also be imbedded in the assembly for the purpose of detection. In this case, the system would pulse the purple light followed by an immediate activation of the array in detection mode to look at the red light. One skilled in the art will appreciate that this concept could also be used to detect other photonics tissue interactions.

Infrared sensors could be used to detect the surface or depth skin temperature to maintain patient safety from skin burns by acting as a dose control parameter during operation of the device. If the tissue gets too hot, the intensity of the light and/or ultrasound could be decreased. Temperature measurement with infrared sensors could also be used to reach or maintain a target tissue temperature (e.g., 38° C. for mild heat, 39° C. for moderate heat, or 41° C. for vigorous heat). The dose of the light and/or ultrasound could be adjusted during treatment to achieve or maintain the target tissue temperature. If it is desired to deliver a fixed level of energy (e.g., 2 joules/cm$^2$) to the tissue, the treatment time could be increased commensurate with the decrease in the dose. The opposite is also true up to the temperature safety limits or to the maximum limit tissue temperature.

Impedance measurement sensors could also be used to control dosage. For example, inflamed tissue is more conductive than non-inflamed tissue. This data may be used to control the dose of the light and/or ultrasound. Typically, if the tissue is more inflamed, the dose of light and/or ultrasound will be decreased. Impedance measurement sensors could also be used to measure skin hydration levels whereby the light and/or ultrasound is actuated until a desired hydration level has been achieved.

Impedance measurement sensors could also be used to determine if the hydrogel layers are correctly attached to the skin and/or are not dried out. Impedance measurement sensors could also be used to identify if the hydrogel used in a treatment is a particular proprietary blend. This may be important from a safety standpoint and/or to ensure that the correct hydrogel is being used in the treatment.

Skin contact and conductive media sensors may be provided to validate that authentic media is being applied and that it is in proper contact with the device and the skin surface to ensure appropriate therapeutic outcomes.

Ultrasonic transmitters and receivers can be used to measure the thickness of the dermis and epidermis, the tissue edema, and the ultrasound attenuation in tissue. This information can be used for dose control of the ultrasonic and light applied by the device.

Figure 15:
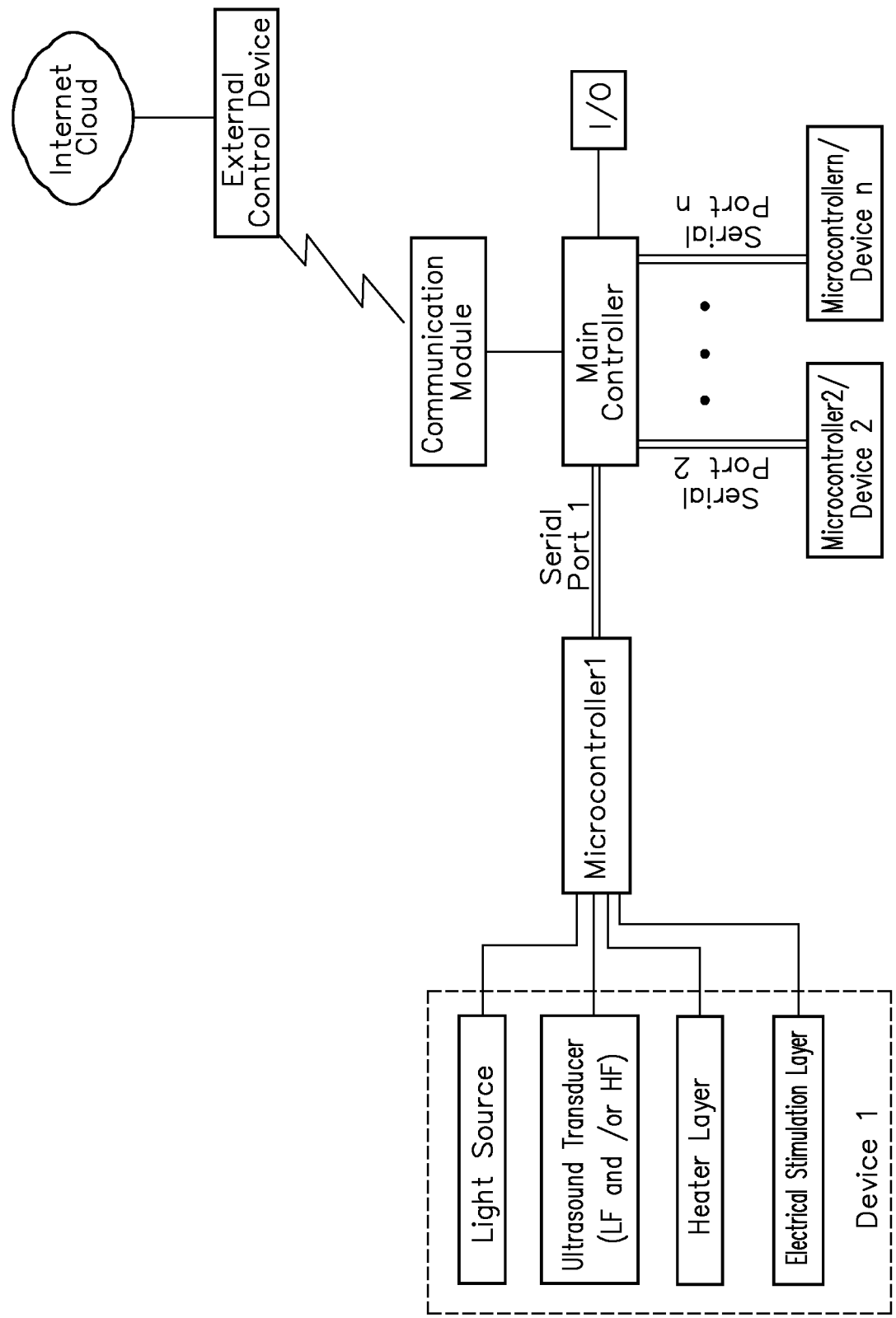
FIG. 15 is a block diagram of a fourth exemplary electronic circuit for controlling a plurality of the devices of the present invention arranged in an array.

In another embodiment, the control module is operable to control a plurality of the devices of the present invention arranged in an array. FIG. 15 is a block diagram of an exemplary electronic circuit for this embodiment. As can be seen, the electronic circuit is similar to that shown and described in connection with FIG. 13, with the addition of a main controller that controls each device in the array. Preferably, each device in the array is assigned a logical address whereby the main controller individually controls the devices through their logical addresses. As such, the main controller may selectively drive each device differently from other devices by, for example, selectively varying a drive voltage or a drive current of the device. In addition, as discussed above, each element of each device may be independently controlled by the associated microcontroller. Thus, the array can be programmed to deliver a desired sequence of light and/or ultrasound frequencies, in pulsed or continuous mode, such that the light and/or ultrasound field moves across the array in a preset pattern and at a preset speed. In addition, the array can be programmed to deliver a desired sequence of heat and/or electrical stimulation in combination with the light and/or ultrasound field.

Various exemplary embodiments of the device of the present invention will now be described.

First Exemplary Embodiment

Figure 4:
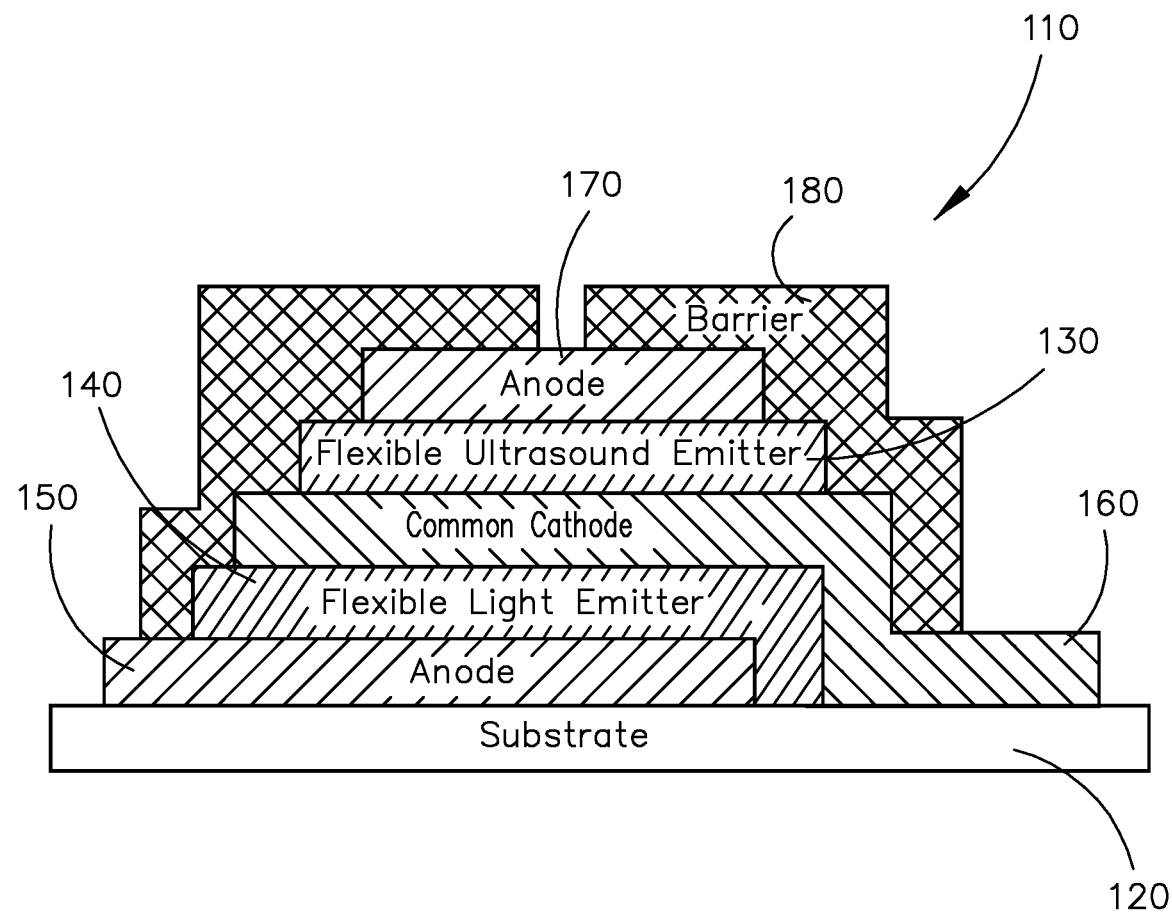
FIG. 4 illustrates a first exemplary embodiment of a device in accordance with the present invention.

FIG. 4 illustrates a first exemplary embodiment of the device of the present invention. The device 110 comprises a light source formed on a transparent substrate 120 and an ultrasonic transducer formed on top of the light source. The light source comprises a flexible light emitter 140 located between an anode 150 and a cathode 160. The ultrasonic transducer comprises a flexible ultrasound emitter 130 located between the cathode 160 (common cathode with the flexible light emitter) and an anode 170. Various power sources are provided so that DC or pulsed DC is used to power the light source, while AC is used to power the ultrasonic transducer. Further, a transparent barrier layer 180 protects the flexible light emitter 140 from moisture and oxygen.

In this exemplary embodiment, the flexible light emitter 140 comprises an OLED or printable LEDs, and the flexible ultrasound emitter 130 comprises PiezoPaint™ material (Meggitt PLC). Both the substrate 120 and the anode 150 are transparent. The substrate is comprised of a transparent silicon rubber, and also serves as a matching layer for the ultrasound. The anode 150 is comprised of ITO. Light generated from the flexible light emitter 140 is emitted through the transparent anode 150 and substrate 120 such that the device has a "bottom" light emitting configuration. Also, the common cathode 160 and the anode 170 are comprised of a conductive metal such as silver. The barrier layer is comprised of Flexent film (Konica Minolta). A therapeutic and/or cosmetic composition as described above may be placed between the substrate 120 and the patient's skin.

Second Exemplary Embodiment

Figure 5:
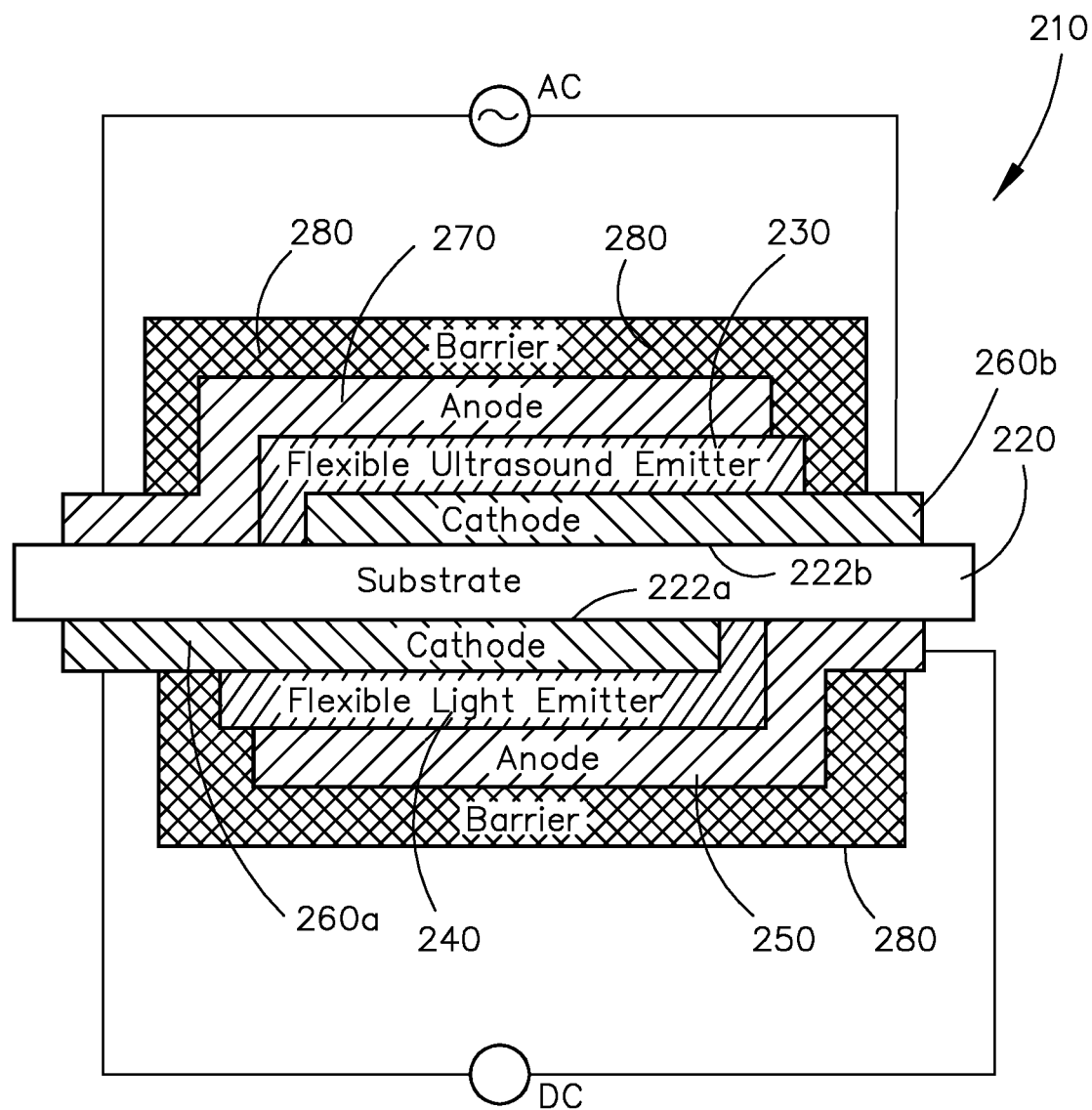
FIG. 5 illustrates a second exemplary embodiment of a device in accordance with the present invention.

FIG. 5 illustrates a second exemplary embodiment of the device of the present invention. The device 210 comprises a light source formed on a first surface 222a of a substrate 220 (i.e., the surface facing towards the patient's skin) and an ultrasonic transducer formed on a second surface 222b of the substrate 220 (i.e., the surface facing away from the patient's skin). The light source comprises a flexible light emitter 240 located between an anode 250 and a cathode 260a. The ultrasonic transducer comprises a flexible ultrasound emitter 230 located between a cathode 260b and an anode 270. Various power sources are provided so that DC or pulsed DC is used to power the light source, while AC is used to power the ultrasonic transducer. Further, a transparent barrier layer 280 protects the flexible light emitter 240 from moisture and oxygen. The barrier layer 280 is formed on the light source, but may optionally also cover the ultrasonic transducer as illustrated.

In this exemplary embodiment, the flexible light emitter 240 comprises an OLED or printable LEDs, and the flexible ultrasound emitter 230 comprises PiezoPaint™ material (Meggitt PLC). The substrate 220 comprises a Mylar film and a silver nanolayer is coated on each side to form the cathode 260a of the light source and the cathode 260b of the ultrasonic transducer. The silver nanolayer is highly reflective to the light generated by the flexible light emitter 240 such that the light is directed towards the skin of the patient. Both the barrier layer 280 and the anode 250 are transparent. The barrier layer 280 is comprised of Willow transparent flexible glass (Dow Corning). The anode 250 is comprised of ITO. Light generated from the flexible light emitter 240 is emitted through the transparent anode 250 and barrier layer 280 such that the device has a "top" light emitting configuration. The anode 270 is comprised of a conductive metal such as silver. A therapeutic and/or cosmetic composition as described above may be placed between the barrier layer 280 and the patient's skin.

Third Exemplary Embodiment

Figure 6:
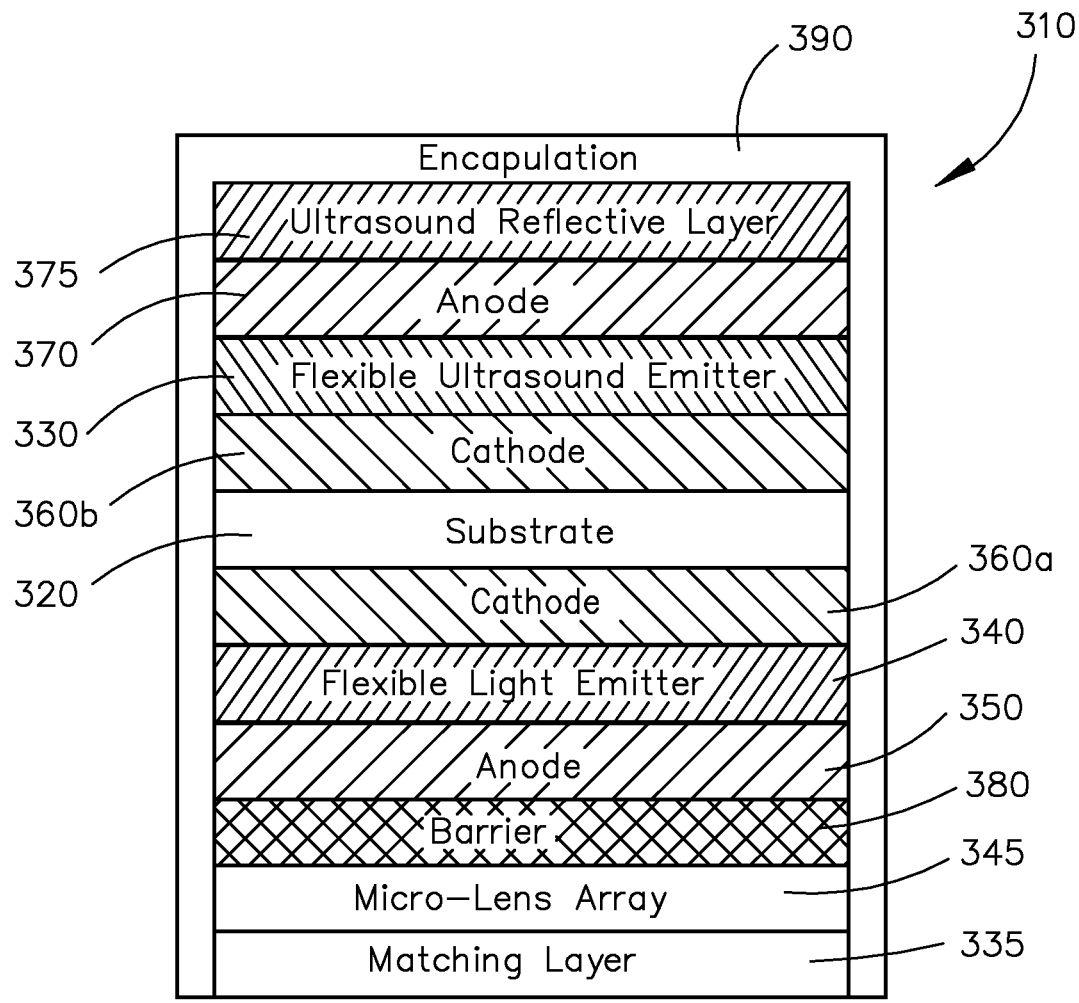
FIG. 6 illustrates a third exemplary embodiment of a device in accordance with the present invention.

FIG. 6 illustrates a third exemplary embodiment of the device of the present invention wherein, for simplicity, the various layers/components of the device are shown in a non-staggered stacked arrangement. This device is the same as the device shown in FIG. 5, but is further modified in one or more of four optional ways, as discussed below.

As with the device shown in FIG. 5, the device 310 includes a light source formed below a substrate 320 and an ultrasonic transducer formed above the substrate 320. The light source comprises a flexible light emitter 340 located between an anode 350 and a cathode 360a. The ultrasonic transducer comprises a flexible ultrasound emitter 330 located between a cathode 360b and an anode 370. Various power sources are provided so that DC or pulsed DC is used to power the light source, while AC is used to power the ultrasonic transducer. For simplicity, the power sources and wiring are not shown. Further, a transparent barrier layer 380 protects the flexible light emitter 340 from moisture and oxygen.

In this exemplary embodiment, the device 310 is optionally modified to include a transparent matching layer 335 located between the ultrasonic transducer and the skin. As discussed above, it will be appreciated that one or more matching layers may be incorporated into the device. Further, the matching layer 335 may include a graphene element (not shown) to provide for heating of the skin. As another option, in this embodiment, an ultrasound reflective layer 375 is located above the transducer, i.e., between the surface of the device facing away from the skin and the ultrasonic transducer. In addition, in this embodiment, the device optionally includes a micro-lens array or scattering layer 345 for improving the output efficiency of the light source. Lastly, in this embodiment, the device is optionally encapsulated in a flexible polymer or silicon rubber 390. A therapeutic and/or cosmetic composition as described above may be placed between the matching layer 335 and the patient's skin.

Fourth Exemplary Embodiment

Figure 7:
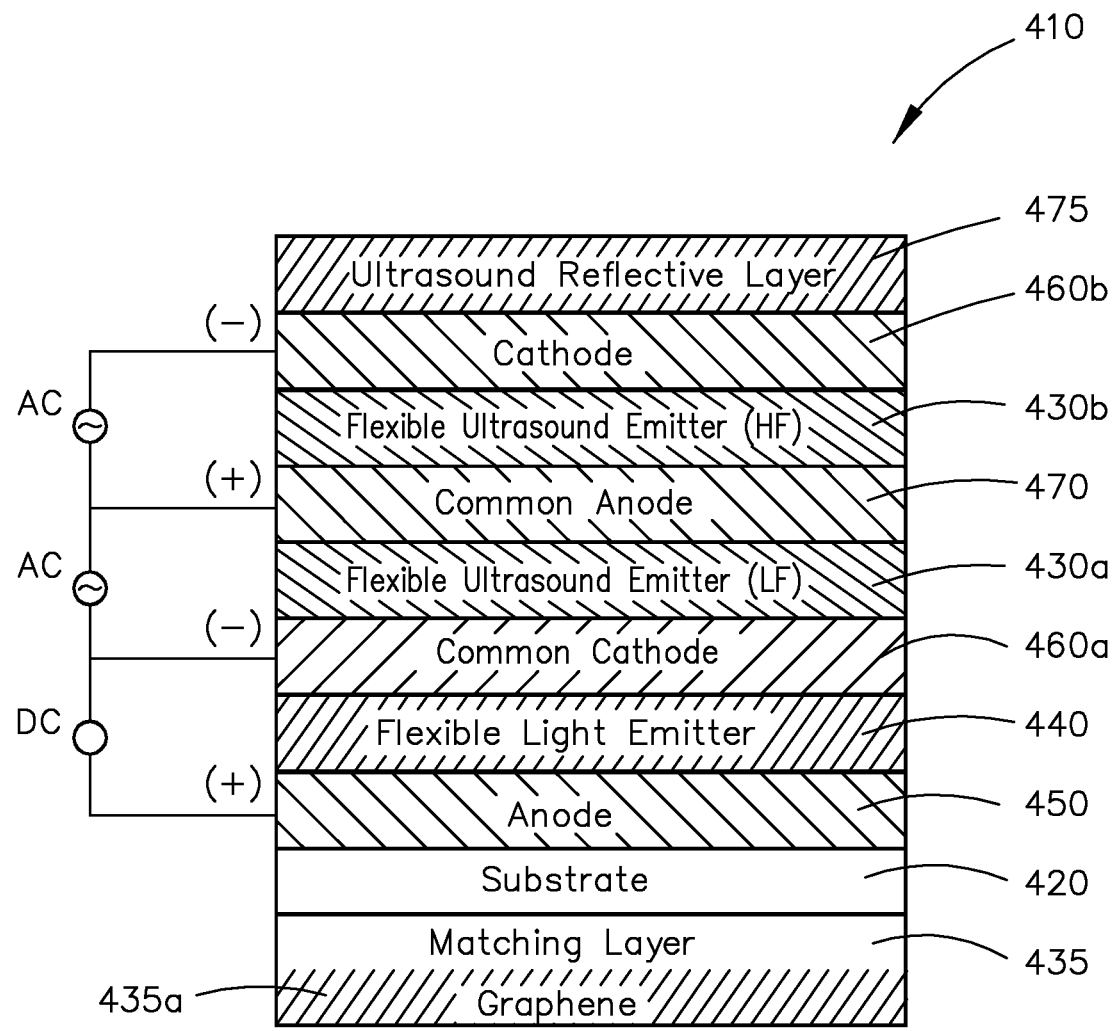
FIG. 7 illustrates a fourth exemplary embodiment of a device in accordance with the present invention.

FIG. 7 illustrates a fourth exemplary embodiment of the device of the present invention wherein, for simplicity, the various layers/components of the device are shown in a non-staggered stacked arrangement. The device 410 comprises a light source formed above a transparent substrate 420 and two ultrasonic transducers formed above the light source. The light source comprises a flexible light emitter 440 located between an anode 450 and a common cathode 460a. The first ultrasonic transducer comprises a flexible low frequency ultrasound emitter 430a located between the cathode 460a (common cathode with the light source) and a common anode 470. The second ultrasonic transducer comprises a flexible high frequency ultrasound emitter 430b located between a cathode 460b and the anode 470 (common anode with the low frequency ultrasound emitter). Various power sources are provided so that DC or pulsed DC is used to power the light source, while AC is used to power each of the ultrasonic transducers.

In this exemplary embodiment, the flexible light emitter 440 comprises an OLED or printable LEDs, and the flexible low frequency 430a and high frequency 430b ultrasound emitters each comprise PiezoPaint™ material (Meggitt PLC) (i.e., the same material is driven at different frequencies). An ultrasound reflective layer 475 is located above the ultrasonic transducers, i.e., between the surface of the device facing away from the skin and the ultrasonic transducers, to direct the ultrasound towards the patient's skin. The ultrasound reflective layer 475 is comprised of ceramic. The anode 470 and cathodes 460a and 460b are each comprised of a conductive metal such as silver. The device further includes a matching layer 435 located between the ultrasonic transducers and the skin. The matching layer 435 has graphene 435a formed therein to serve as a flexible heater layer. The graphene 435a may also serve as an electrical stimulation layer for iontophoresis.

The anode 450, substrate 420, and matching layer 435 with graphene 435a are all transparent. The substrate 420 is comprised of a transparent silicon rubber, and also serves as a matching layer for the ultrasound. The anode 450 is comprised of ITO. Light generated from the flexible light emitter 440 is emitted through the transparent anode 450, substrate 420 and matching layer 435 with graphene 435a such that the device has a "bottom" light emitting configuration. A therapeutic and/or cosmetic composition as described above may be placed between the matching layer 435 with graphene 435a and the patient's skin.

Fifth Exemplary Embodiment

Figure 8:
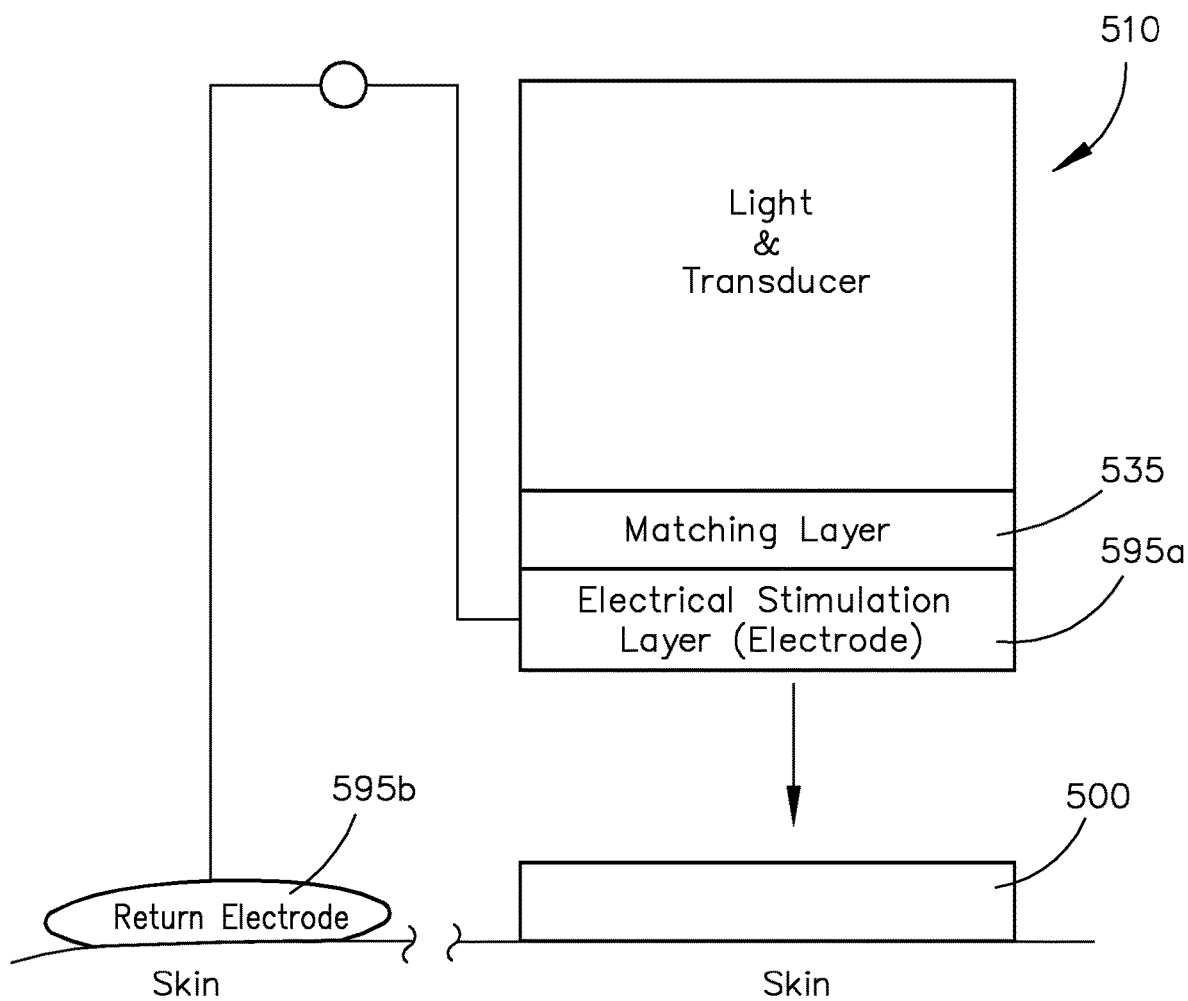
FIG. 8 illustrates a fifth exemplary embodiment of a device in accordance with the present invention.

FIG. 8 illustrates a fifth exemplary embodiment of the device of the present invention. The device 510 comprises a light/transducer structure (e.g., having a layered configuration as illustrated in one of the prior embodiments), along with a matching layer 535 and a transparent negative electrode that serves as an electrical stimulation layer 595a for providing optional electrical stimulation to the patient. The electrical stimulation layer is electrically coupled to a positive return electrode 595b applied to the surface of the skin at a separate location. Electrical current flows from a power source to the positive return electrode 595b and through the patient's skin to the negative electrode 595a. The current is preferably a DC current of about 1 to 10 mA (e.g., about 1, 2, 3, 4, 5, 6, 7, 8, 9, or 10 mA) with about 2 to 4 mA being most preferred. The voltage is typically 100 V or less (e.g., about 100, 90, 80, 70, 60, 50 or 40 V or less). A therapeutic and/or cosmetic composition 500 as described above is placed between the electrical stimulation layer 595a and the patient's skin.

Sixth Exemplary Embodiment

Figure 9:
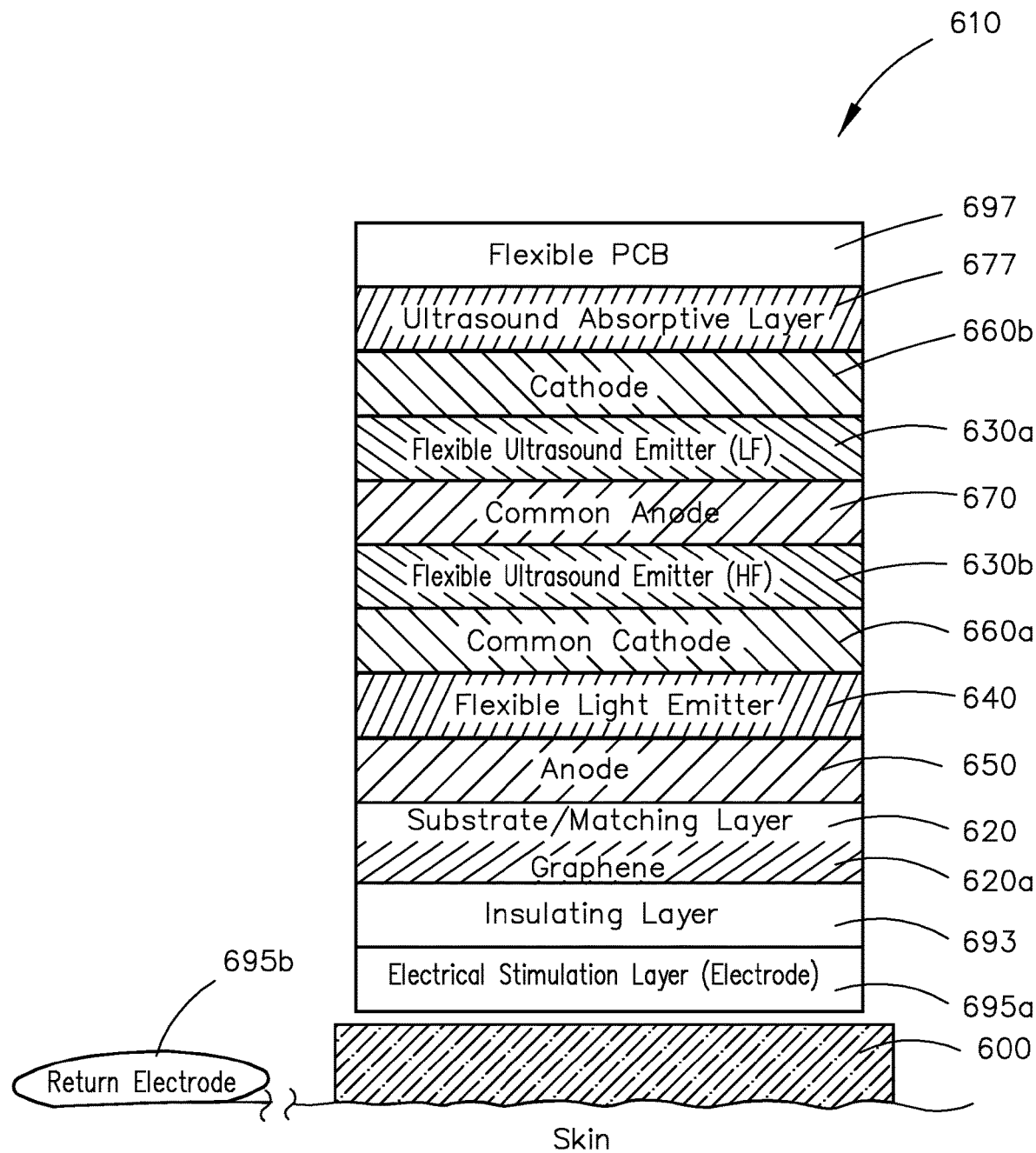
FIG. 9 illustrates a sixth exemplary embodiment of a device in accordance with the present invention.

FIG. 9 illustrates a sixth exemplary embodiment of the device of the present invention wherein, for simplicity, the various layers/components of the device are shown in a non-staggered stacked arrangement. The device 610 comprises a light source formed above a transparent substrate 620, which also functions as a matching layer as described below. Two ultrasonic transducers are formed above the light source. The light source comprises a flexible light emitter 640 located between an anode 650 and a common cathode 660a. The first ultrasonic transducer comprises a flexible high frequency ultrasound emitter 630b located between the cathode 660a (common cathode with the light source) and a common anode 670. The second ultrasonic transducer comprises a flexible low frequency ultrasound emitter 630a located between a cathode 660b and the anode 670 (common anode with the high frequency transducer). Various power sources are provided so that DC or pulsed DC used to power the light source, while AC is used to power each of the ultrasonic transducers.

In this exemplary embodiment, an ultrasonic absorptive layer 677 is located above the ultrasonic transducers, i.e., between the surface of the device facing away from the skin and the ultrasonic transducers, to absorb ultrasound in that direction. The common anode 670 and cathodes 660a and 660b are each comprised of a conductive metal such as silver. As noted above, the substrate 620 located between the ultrasonic transducers and the skin also serves as a matching layer. The substrate/matching layer 620 has graphene 620a formed therein to serve as a heater layer. Further, the device includes a positive electrode that serves as an electrical stimulation layer 695a for providing optional electrical stimulation to the patient. The electrical stimulation layer 695a is electrically coupled to a negative return electrode 695b applied to the surface of the skin at a separate location. Electrical current flows from a power source to the positive electrode 695a and through the patient's skin to the negative return electrode 695b. An insulating layer 693 may be provided between the substrate/matching layer 620 with graphene 620a and the electrical stimulation layer 695a. A therapeutic and/or cosmetic composition 600 as described above is placed between the electrical stimulation layer 695*a* and the patient's skin.

In this exemplary embodiment, the flexible light emitter 640 comprises an OLED or printable LEDs, and the flexible low and high frequency ultrasound emitters 630*a*, 630*b* each comprise PiezoPaint™ material (Meggitt PLC) (i.e., the same material is driven at different frequencies). The anode 650, substrate/matching layer 620 with graphene 620*a*, insulating layer 693 and electrical stimulation layer 695*a* are all transparent. The anode 650 is comprised of ITO. The substrate/matching layer 620 is comprised of a transparent silicon rubber. The insulating layer 693 is formed of transparent silicon, and the electrical stimulation layer 695*a* is formed of conductive transparent silicon, graphene, or transparent silver fiber. Light generated from the flexible light emitter 640 is emitted through the transparent anode 650, substrate/matching layer 620 with graphene 620*a*, insulating layer 693 and electrical stimulation layer 695*a* such that the deviced has a "bottom" light emitting configuration.

Also, in this exemplary embodiment, a flexible printed circuit board (PCB) 697 is printed on the surface of the device facing away from the patient's skin. The flexible PCB 697 contains the electrical components shown generally in FIG. 14, including the microcontroller (with drive circuits for the light source, ultrasonic transducers, and electrical stimulation layer), the wireless communication module (e.g., Wi-Fi or Bluetooth), the sensor electronics. The flexible PCB 697 is electrically coupled to a photo sensor in contact with the patient's skin. The light source pulses the patient's skin with purple light (e.g., 415 nm) and the photo sensor measures the presence of acne bacterium by detecting red light (e.g., 630 nm) given off by acne bacterium. The feedback provided by the photo sensor is used by the flexible PCB 697 to vary or terminate the dose based on the bacterial kill rate.

Seventh Exemplary Embodiment

Figure 10:
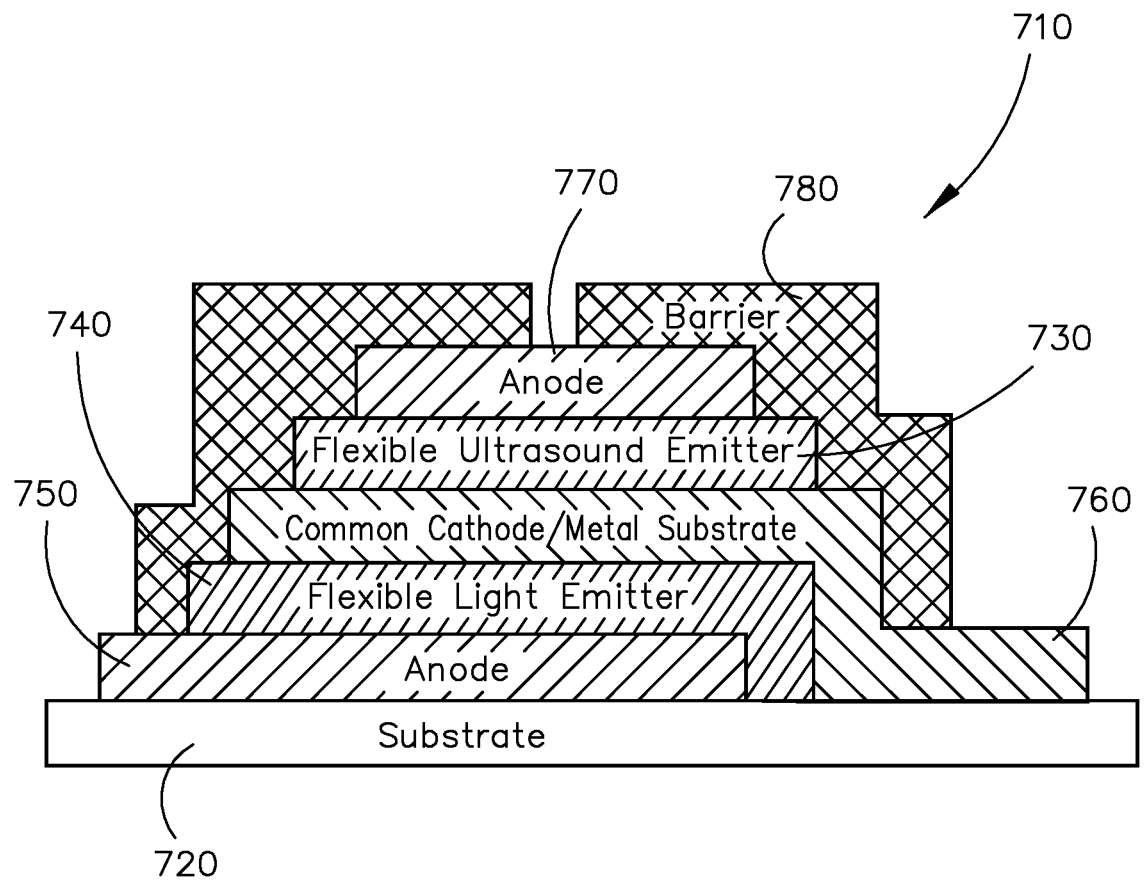
FIG. 10 illustrates a seventh exemplary embodiment of a device in accordance with the present invention.

FIG. 10 illustrates a seventh exemplary embodiment of the device of the present invention. The device 710 comprises a light source formed above a transparent substrate 720 and a dual frequency ultrasonic transducer formed above the light source (i.e., a dual frequency transducer with a unimorph design, as discussed above). The light source comprises a flexible light emitter 740 located between an anode 750 and a common cathode 760. The dual frequency ultrasonic transducer comprises a flexible ultrasound emitter 730 bonded to a metal substrate 760 as described in Galluzzo et al., U.S. Published Patent Application No. 2012/0267986. The metal substrate 760 functions as the cathode for the flexible ultrasound emitter 730 (common cathode with the light source) and an anode 770 is also provided. Various power sources are provided so that DC or pulsed DC is used to power the light source, while AC is used to power the dual frequency ultrasonic transducer. For simplicity, the power sources and wiring are not shown. Further, a transparent barrier layer 780 protects the flexible light emitter 740 from moisture and oxygen.

In this exemplary embodiment, the flexible light emitter 740 comprises an OLED or printable LEDs, and the flexible ultrasound emitter 730 comprises PiezoPaint™ material (Meggitt PLC) (which can function as a dual frequency transducer with a unimorph design). Both the substrate 720 and the anode 750 are transparent. The substrate is comprised of a transparent silicon rubber, and also serves as a matching layer for the ultrasound. The anode 750 is comprised of ITO. Light generated from the flexible light emitter 740 is emitted through the transparent anode 750 and substrate 720 such that the device has a "bottom" light emitting configuration. The metal substrate 760 (common cathode to the light source and transducer) is made of stainless steel, and the anode 770 is comprised of a conductive metal such as silver. The barrier layer is comprised of Flexent film (Konica Minolta). A therapeutic and/or cosmetic composition as described above is placed between the substrate 720 and the patient's skin.

Eighth Exemplary Embodiment

Figure 11:
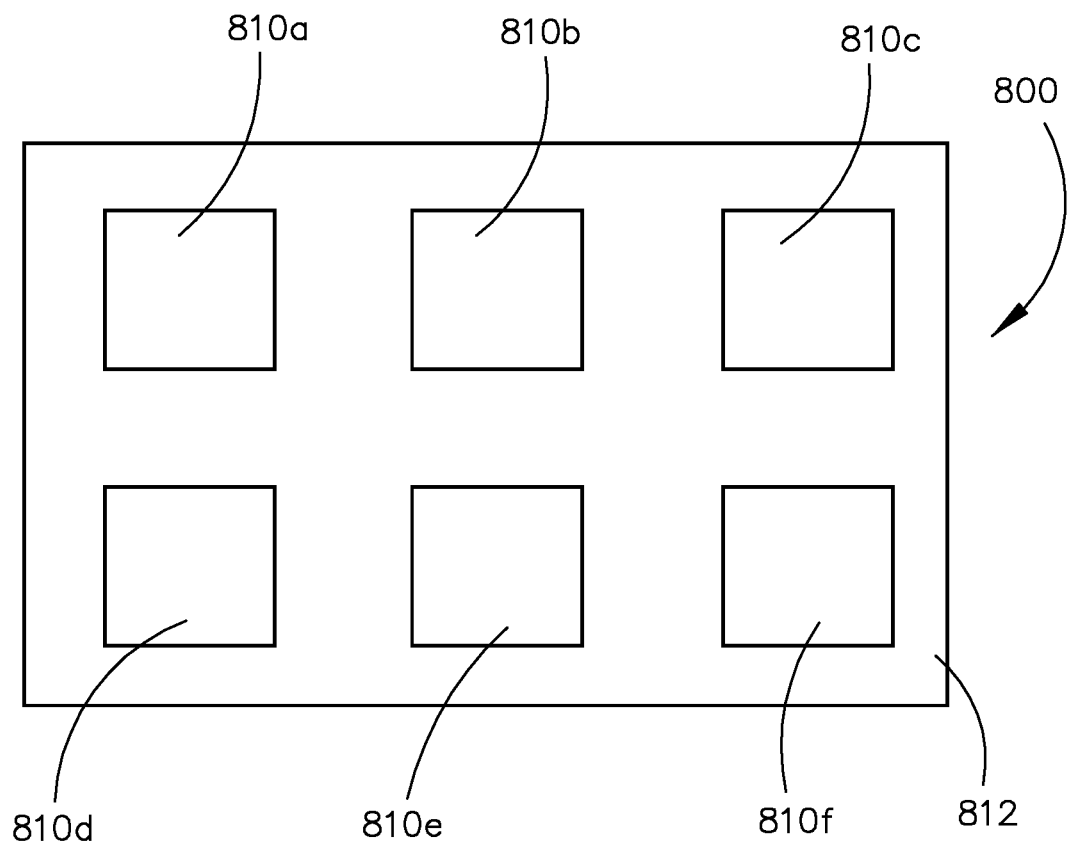
FIG. 11 illustrates an eighth exemplary embodiment of a system comprising a plurality of the devices of the present invention arranged in an array.

FIG. 11 illustrates an eighth exemplary embodiment of a light/ultrasonic transducer system 800 in accordance with the present invention. The light/ultrasonic transducer system 800 comprises a plurality of devices 810*a*-810*f* each of which may be configured in accordance with any one of the previous exemplary embodiments. The devices are arranged in an array and held in proximity to each other by a flexible, preferably transparent, material 812, such as a silicon or plastic, or other polymer. In this exemplary embodiment, six devices are generally illustrated. However, it will be appreciated that the system may include any number of devices (e.g., 2, 4, 6, 8, 10, 12, 14, 16, 18, 20, 30, 40, 50, etc.) arranged in an array. The devices are individually connected to one or more power sources (not shown). It should be noted that each array element could have different output parameters for the ultrasound and light based on sensing information recorded from the tissue underlying each section of the array.

The devices 810*a*-810*f* may be the same or different, for example in terms of the shape, size, light output and/or ultrasonic output. The devices may emit light of different wavelengths, intensities, durations, duty factors, and modulation frequencies. The devices may produce ultrasound of different frequencies, power densities, modulation frequencies, and duty factors. Each of the devices may be independently controlled by a microcontroller, and, each light source and/or ultrasonic transducer within each of the devices may be independently controlled by the microcontroller. As such, each of the devices is capable of delivering light and/or ultrasound simultaneously or sequentially or separately.

While the present invention has been described and illustrated hereinabove with reference to several exemplary embodiments, it should be understood that various modifications could be made to these embodiments without departing from the scope of the invention. Therefore, the present invention is not to be limited to the specific configuration and methodology of the exemplary embodiments, except insofar as such limitations are included in the following claims.

What is claimed and desired to be secured by Letters Patent is as follows:

1. A flexible device having a layered structure for delivering electrical stimulation, light and ultrasound to a skin surface, comprising:
   a plurality of flexible conductive layers configured to connect to a power source,
   wherein the flexible conductive layers comprise a first conductive layer, a second conductive layer, and a third conductive layer;
   (a) a flexible light emitter layer positioned between the first conductive layer and the second conductive layer, wherein the flexible light emitter layer comprises a layer of printed light emitting diodes configured to emit light when driven by the power source, wherein the layer of printed light emitting diodes comprises a plurality of individual light emitting diodes suspended and dispersed in a liquid or gel so as to form a diode ink that is printed on one of the first and second conductive layers and wherein the other of the first and second conductive layers is applied over the diode ink, wherein the first conductive layer comprises a transparent conductive layer such that the light passes through the transparent conductive layer to the skin surface and (b) a flexible ultrasound emitter layer positioned between the second conductive layer and the third conductive layer, wherein the flexible ultrasound emitter layer is configured to produce ultrasound when driven by the power source; and a flexible electrical stimulation layer configured to connect to the power source, wherein the flexible electrical stimulation layer is configured to function as an electrode and provide electrical stimulation when driven by the power source.

2. The device of claim 1, wherein the flexible electrical stimulation layer is configured to function as one of the flexible conductive layers.

3. The device of claim 1, wherein the flexible electrical stimulation layer is transparent such that the light passes through the flexible electrical stimulation layer to the skin surface.

4. The device of claim 1, wherein the electrical stimulation provided by the flexible electrical stimulation layer is configured to iontophoretically deliver a charged therapeutic or cosmetic composition through the skin surface.

5. The device of claim 1, wherein the electrical stimulation provided by the flexible electrical stimulation layer is configured to decrease muscle spasms.

6. The device of claim 1, wherein the electrical stimulation provided by the flexible electrical stimulation layer is configured to decrease muscle tone for the treatment of muscle hypertonicity.

7. The device of claim 1, wherein the electrical stimulation provided by the flexible electrical stimulation layer is configured to increase muscle tone for the treatment of muscle hypotonicity.

8. The device of claim 1, wherein the electrical stimulation provided by the flexible electrical stimulation layer is configured to provide electroanesthesia.

9. The device of claim 1, wherein one or both of the light emitted by the flexible light emitter layer and the ultrasound produced by the flexible ultrasound emitter layer is configured to cause transdermal transport of a therapeutic or cosmetic composition through the skin surface.

10. The device of claim 1, wherein the flexible ultrasound emitter layer comprises a piezoelectric coating.

11. The device of claim 1, wherein the flexible ultrasound emitter layer is configured to produce one or both of low frequency ultrasound at a frequency in the range of 20 kHz to 500 kHz and high frequency ultrasound at a frequency in the range of 500 kHz to 20 MHz.

12. The device of claim 1, further comprising a flexible heater layer.

13. The device of claim 1, further comprising a flexible printed circuit board layer.

14. The device of claim 1, further comprising a flexible acoustic matching layer.

15. The device of claim 1, wherein the device is flexible and configured to form a non-planar contact surface against the skin surface.

16. The device of claim 1, wherein the device is conformable to the skin surface.

17. A system for delivering electrical stimulation, and one or both of light and ultrasound to a skin surface, comprising:
the flexible device of claim 1; and
a flexible device comprising:
a plurality of flexible conductive layers configured to connect to a power source, wherein the flexible conductive layers comprise a first conductive layer, a second conductive layer, and a third conductive layer;
(a) a flexible light emitter layer positioned between the first conductive layer and the second conductive layer, wherein the flexible light emitter layer comprises a layer of printed light emitting diodes configured to emit light when driven by the power source, wherein the layer of printed light emitting diodes comprises a plurality of individual light emitting diodes suspended and dispersed in a liquid or gel so as to form a diode ink that is printed on one of the first and second conductive layers and wherein the other of the first and second conductive layers is applied over the diode ink, wherein the first conductive layer comprises a transparent conductive layer such that the light passes through the transparent conductive layer to the skin surface and (b) a flexible ultrasound emitter layer positioned between the second conductive layer and the third conductive layer, wherein the flexible ultrasound emitter layer is configured to produce ultrasound when driven by the power source;
a flexible electrical stimulation layer configured to connect to the power source, wherein the flexible electrical stimulation layer is configured to function as an electrode and provide electrical stimulation when driven by the power source; and
an electronic circuit electrically coupled to the flexible device, wherein the electronic circuit comprises a controller operable to control the flexible device.

18. The system of claim 17, wherein the controller is electrically coupled to at least one sensor in contact with the skin surface, wherein the controller is operable to receive sensor data from the sensor and dynamically control the flexible device in response to the received sensor data.

19. The system of claim 17, wherein the controller is electrically coupled to a communication module that enables wired or wireless communication with an external control device.

20. The system of claim 19, wherein the external control device is operable to execute a control application for externally controlling the controller.

21. The system of claim 19, wherein the external control device is operable to communicate with a remote server.

22. The system of claim 17, further comprising a therapeutic or cosmetic composition configured to be applied to the skin surface.

23. The system of claim 22, wherein the composition is in the form of a gel, cream or ointment, or a pad incorporating a gel, cream or ointment.

24. The system of claim 22, wherein the composition is contained in a hydrogel pad.

25. The system of claim 22, wherein the composition includes a conductive ionic molecule or compound.

26. The system of claim 25, wherein the electrical stimulation provided by the flexible electrical stimulation layer is configured to iontophoretically deliver the conductive ionic molecule or compound through the skin surface.

27. The system of claim 26, wherein the conductive ionic molecule or compound is positively charged, and wherein the power source is configured to connect to the flexible electrical stimulation layer and a return electrode such that the flexible electrical stimulation layer is configured to function as a positive electrode and the return electrode is configured to function as a negative electrode.

28. The system of claim 26, wherein the conductive ionic molecule or compound is negatively charged, and wherein the power source is configured to connect to the flexible electrical stimulation layer and a return electrode such that the flexible electrical stimulation layer is configured to function as a negative electrode and the return electrode is configured to function as a positive electrode.

29. The system of claim 22, wherein the composition includes one or more of low or high molecular weight hyaluronic acid, ascorbic acid (vitamin C) or alpha-tocopherol (vitamin E) or their derivatives or their pharmaceutically acceptable salts and esters.

30. The system of claim 29, wherein one or both of the light emitted by the flexible light emitter layer and the ultrasound produced by the flexible ultrasound emitter layer is configured to cause transdermal transport of the composition through the skin surface.

31. The system of claim 17, wherein the power source is operable to generate a current to drive the flexible electrical stimulation layer, wherein the current comprises one of a direct current, an alternating current, a pulsed direct current, or a direct current superimposed with one of an alternating current or a pulsed direct current.

32. The system of claim 17, wherein the power source is operable to generate a current to drive the flexible light emitter layer, wherein the current comprises one of a direct current or a pulsed direct current.

33. The system of claim 17, wherein the power source is operable to generate a current to drive the flexible ultrasound emitter layer, wherein the current comprises an alternating current.

34. The system of claim 17, further comprising a return electrode configured to be applied to the skin surface at a location separate from the device, wherein the power source is configured to be connected to the flexible electrical stimulation layer and the return electrode so as to provide the electrical stimulation.

35. The system of claim 17, further comprising a return electrode incorporated into the flexible device, wherein the power source is configured to be connected to the flexible electrical stimulation layer and the return electrode so as to provide the electrical stimulation.

36. The system of claim 17, wherein the electrical stimulation provided by the flexible electrical stimulation layer is configured to decrease muscle spasms.

37. The system of claim 17, wherein the electrical stimulation provided by the flexible electrical stimulation layer is configured to decrease muscle tone for the treatment of muscle hypertonicity.

38. The system of claim 17, wherein the electrical stimulation provided by the flexible electrical stimulation layer is configured to increase muscle tone for the treatment of muscle hypotonicity.

39. The system of claim 17, wherein the electrical stimulation provided by the flexible electrical stimulation layer is configured to provide electroanesthesia.

40. The system of claim 17, wherein the flexible ultrasound emitter layer comprises a piezoelectric coating.

41. The system of claim 17, wherein the device is conformable to the skin surface.

42. A flexible device having a layered structure for delivering electrical stimulation, light and ultrasound to a skin surface, comprising:

a plurality of flexible conductive layers configured to connect to a power source, wherein the flexible conductive layers comprise a first conductive layer, a second conductive layer, and a third conductive layer;

(a) a flexible light emitter layer positioned between the first conductive layer and the second conductive layer two, wherein the flexible light emitter layer comprises one of an organic light emitting diode or a plurality of printed light emitting diodes comprising a plurality of individual light emitting diodes suspended and dispersed in a liquid or gel so as to form a diode ink that is printed on one of the flexible conductive layers, wherein the flexible light emitter layer is configured to emit light when driven by the power source, wherein the first conductive layer comprises a transparent conductive layer such that the light passes through the transparent conductive layer to the skin surface and (b) a flexible ultrasound emitter layer positioned between the second conductive layer and the third conductive layer, wherein the flexible ultrasound emitter layer is configured to produce ultrasound when driven by the power source; and a flexible electrical stimulation layer configured to connect to the power source, wherein the flexible electrical stimulation layer is configured to function as an electrode and provide electrical stimulation when driven by the power source.

43. The device of claim 42, wherein the flexible electrical stimulation layer is transparent such that the light passes through the flexible electrical stimulation layer to the skin surface.

44. The device of claim 42, wherein at least one of the flexible conductive layers comprises a transparent conductive layer such that the light passes through the transparent conductive layer to the skin surface.

45. The device of claim 42, wherein the flexible ultrasound emitter layer comprises a piezoelectric coating.

46. A flexible device having a layered structure for delivering electrical stimulation, light and ultrasound to a skin surface, comprising:

a plurality of flexible conductive layers configured to connect to a power source, wherein the flexible conductive layers comprise a first conductive layer, a second conductive layer, a third conductive layer, and a fourth conductive layer;

(a) a flexible light emitter layer positioned between the first conductive layer and the second conductive layer, wherein the flexible light emitter layer comprises one of an organic light emitting diode or a plurality of printed light emitting diodes comprising a plurality of individual light emitting diodes suspended and dispersed in a liquid or gel so as to form a diode ink that is printed on one of the flexible conductive layers, wherein the flexible light emitter layer is configured to emit light when driven by the power source, wherein the first conductive layer comprises a transparent conductive layer such that the light passes through the transparent conductive layer to the skin surface and (b) a flexible ultrasound emitter layer positioned between the third conductive layer and the fourth conductive layer, wherein the flexible ultrasound emitter layer is configured to produce ultrasound when driven by the power source; and a flexible electrical stimulation layer configured to connect to the power source, wherein the flexible electrical stimulation layer is configured to function as an electrode and provide electrical stimulation when driven by the power source.

\* \* \* \* \*

UNITED STATES PATENT AND TRADEMARK OFFICE
CERTIFICATE OF CORRECTION

PATENT NO. : 11,083,619 B2
APPLICATION NO. : 15/382795
DATED : August 10, 2021
INVENTOR(S) : Michael R. Hall, John C. Castel and Dawn Castel Page 1 of 1

It is certified that error appears in the above-identified patent and that said Letters Patent is hereby corrected as shown below:

In the Claims

Column 46
Line 7, delete "two" between "layer" and ", wherein".

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*